United States Patent [19]

Kirsch et al.

[11] Patent Number: 5,798,365

[45] Date of Patent: Aug. 25, 1998

[54] SUBSTITUTED QUINOLINE DERIVATIVES, A PROCESS FOR THEIR PREPARATION, AND THEIR USE

[75] Inventors: Reinhard Kirsch, Brunswick; Jörg-Peter Kleim, Kelkheim; Günther Riess, Hattersheim; Manfred Rösner, Eppstein; Irvin Winkler, Liederbach, all of Germany

[73] Assignee: Hoechst Aktiengesellschaft, Frankfurt am Main, Germany

[21] Appl. No.: 515,556

[22] Filed: Aug. 14, 1995

[30] Foreign Application Priority Data

Aug. 16, 1994 [DE] Germany .................. 44 28 932.4

[51] Int. Cl.$^6$ .................. C07D 215/227; C07D 215/38; A61K 31/47

[52] U.S. Cl. .................. 514/312; 514/313; 546/158; 546/159

[58] Field of Search .................. 546/158, 159; 514/312, 313

[56] References Cited

FOREIGN PATENT DOCUMENTS 0 579 968 A1  1/1994  European Pat. Off. .
41 42 322     7/1993  Germany .
92/16508     10/1992  WIPO .

OTHER PUBLICATIONS

Lewis, J Org Chem, vol. 56, No. 18, pp. 5311–5318, 1991.
Himbert, Chem Ber., vol. 122, pp. 1161–1173, 1989.
Hirsch, "Aids Commentary", The Journal of Infectious Diseases, 157(3):427–431 (1988).
Coppola, "The Chemistry of Isatoic Anhydride", Synthesis, pp. 505–536, 1980.
Kaneko, C. et al., Photochemistry of Heterocyclic Compounds. (4) .[1]) Solvent Effects in the Photolysis of Tetrahydroacridine 10–Oxide Derivatives[2]), Chem. Pharm. Bull., 17:1290–1294(1969).

Searles et al., The Preparation of α,α-Dialkylacetoacetanilides and Their Reaction with Sulfuric Acid, J. Am. Chem. Soc., 78:2242–2246 (1956).
Daruwala et al., "β–Amino Ketones. Synthesis and Some Biological Activities in Mice of 3,3-Dialkyl-1,2,3, 4-Tetrahydro-4-quinolinones and Related Mannich Bases", Journal of Medicinal Chemistry, 17(8):819–824(1974).
F.D. Lewis et al., "Spectroscopy and Photochemistry of 2-Quinolones and Their Lewis Acid Complexes," J. Org. Chem., vol. 56, No. 18, (1991), pp. 5311–5318.
G. Himbert et al., "Influence Of Substituents In p–, m–, and o–Position Of The Arene Onto The Intramolecular Diels–Adler Reaction of Allenecarboxylic Acid Anilides and Phenyl Esters," Chem. Ber., vol. 122, No. 6, (1989), pp. 1161–1173.

Primary Examiner—Bernard Dentz
Assistant Examiner—D. Margaret M. Mach
Attorney, Agent, or Firm—Finnegan, Henderson, Farabow, Garrett & Dunner, L.L.P.

[57] ABSTRACT

Compounds of the formula I,

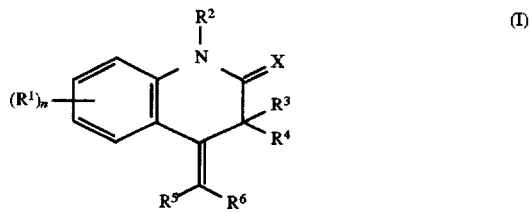

(I)

and also their tautomeric forms of the formula Ia,

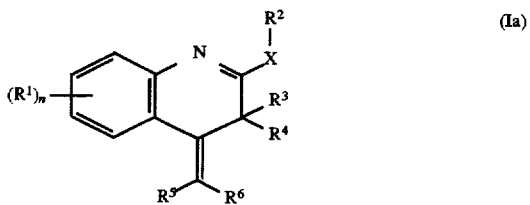

(Ia)

in which the substituents $R^1$ to $R^6$ and X have said meanings, exhibit antiviral activity.

10 Claims, No Drawings

SUBSTITUTED QUINOLINE DERIVATIVES, A PROCESS FOR THEIR PREPARATION, AND THEIR USE

The present invention relates to alkylene-substituted quinoline derivatives, to a process for their preparation and to their use.

Viral infections are widespread in humans and animals, in particular in humans. However, despite intensive efforts, success has not so far been achieved in finding chemotherapeutic agents which successfully interfere to any substantial degree, causatively or symptomatically, with the disease process induced by viruses or retroviruses. For this reason, viral, and, in particular, retroviral, diseases can only be treated very incompletely with chemotherapeutic agents. Owing to the rapidly increasing number of people who are infected with the HIV virus worldwide, this type of retroviral virus infection, in particular, represents a growing global problem.

The retrovirus designated human immunodeficiency virus (HIV) is presumed, inter alia, to be the causative agent of the complex disease known as AIDS (acquired immune deficiency syndrome). AIDS causes a progressive destruction of the immune system of the sufferer which is associated with destruction of the peripheral and central nervous system. Reverse transcription of the RNA genome of the virus, which is carried out by the virus' own reverse transcriptase enzyme and which provides DNA copies of the HIV sequence, represents an important step in the replication cycle of retroviruses. It is known that some compounds, for example azidothymidine (AZT), can function as inhibitors of the reverse transcriptase. They are therefore used for treating AIDS. However, AZT and similar compounds of the nucleoside type, such as DDC or DDI, either have a very narrow therapeutic range or exhibit severe toxicity which can already be seen within the therapeutic range (see, for example, Hirsch, M. S. (1988) J. Infect. Dis. 157, 427–431). Furthermore, the problem of the development of resistance towards chemotherapeutic agents has still not been solved.

Patent Application EP 93 109 965.9 describes iminoquinoline derivatives which possess antiviral activity against the HIV virus. Patent Application EP 93 109 965.9 describes quinoxalinone derivatives which have related structures and which possess antiviral activity. In addition, the compounds A and B are known (see Kaneko, C. et al., Chem. Pharm. Bull., 17 (1969), 1290–1294 and Searles and Kelly, J. Am. Chem. Soc., 78 (1956), 2242–2243); however, these two derivatives have not yet been reported to have any antiviral effect.

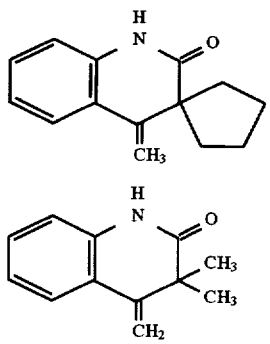

There has also been no report of antivirally active derivatives which differ from the said iminoquinoline compounds in that substituents are bound in the 4 position of the heterocyclic quinoline ring system by way of a C—C double bond.

It has now been found, surprisingly, that certain 4-alkylene-substituted quinoline derivatives exhibit a high degree of antiviral activity, in particular against human immunodeficiency virus (HIV).

Accordingly, the subject matter of the invention are compounds of the formula I,

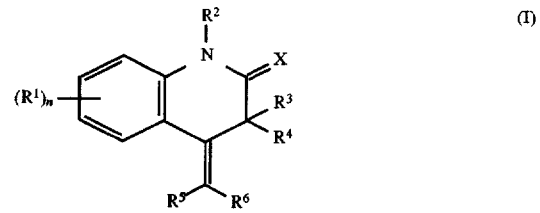

and also their tautomeric forms of the formula Ia,

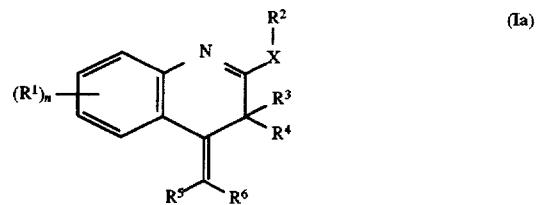

in which:

1) n is zero, one, two, three or four, the individual substituents $R^1$ are, independently of each other, fluorine, chlorine, bromine, iodine, trifluoromethyl, trifluoromethoxy, hydroxyl, alkyl, cycloalkyl, alkoxy, alkoxy(alkoxy), alkylthio, alkylsulfinyl, alkylsulfonyl, nitro, amino, azido, alkylamino, dialkylamino, piperidino, morpholino, 1-pyrrolidinyl, acyl, acyloxy, acylamino, cyano, carbamoyl, carboxyl, alkyloxycarbonyl, hydroxysulfonyl or sulfamoyl, or a phenyl, phenoxy, phenoxycarbonyl, phenylthio, phenylsulfinyl, phenylsulfonyl, phenoxysulfonyl, phenylsulfonyloxy, anilinosulfonyl, phenylsulfonylamino, benzoyl, heteroaroyl, heteroaryl, heteroarylmethyl, heteroarylmethyloxy or heteroarylmethylthio radical which is optionally substituted by up to five radicals $R^7$ which are independent of each other, where $R^7$ can be fluorine, chlorine, bromine, iodine, cyano, trifluoromethyl, trifluoromethoxy, nitro, amino, azido, alkyl, cycloalkyl, alkoxy, alkylthio, alkylsulfinyl, alkylsulfonyl, alkylamino, dialkylamino, alkyloxycarbonyl, phenyl, phenoxy or heteroaryl, X is oxygen, sulfur, selenium or substituted nitrogen N—$R^2$ or N—O—$R^2$, where $R^2$ is hydrogen or alkyl which is optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl or alkoxycarbonyl;

alkenyl which is optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

alkynyl which is optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

cycloalkyl which is optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

cycloalkenyl which is optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

(cycloalkyl)-(alkyl) which is optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

(cycloalkenyl)-(alkyl) which is optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

alkylcarbonyl which is optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

alkenylcarbonyl which is optionally substituted by fluorine, chlorine or hydroxyl, alkoxy, oxo or phenyl;

(cycloalkyl)carbonyl which is optionally substituted by fluorine, chlorine or hydroxyl, alkoxy, oxo or phenyl;

(cycloalkenyl)carbonyl which is optionally substituted by fluorine, chlorine or hydroxyl, alkoxy, oxo or phenyl;

(cycloalkyl)-(alkyl)carbonyl which is optionally substituted by fluorine, chlorine or hydroxyl, alkoxy, oxo or phenyl;

(cycloalkenyl)-(alkyl)carbonyl which is optionally substituted by fluorine, chlorine or hydroxyl, alkoxy, oxo or phenyl;

alkyloxycarbonyl which is optionally substituted by fluorine, chlorine, bromine, hydroxyl, alkoxy, alkylamino, dialkylamino or alkylthio;

alkenyloxycarbonyl which is optionally substituted by fluorine, chlorine, hydroxyl, alkoxy, oxo or phenyl;

alkynyloxycarbonyl which is optionally substituted by fluorine, chlorine, hydroxyl, alkoxy, oxo or phenyl;

alkylthiocarbonyl which is optionally substituted by fluorine, chlorine, hydroxyl, alkoxy, oxo or phenyl;

alkenylthiocarbonyl which is optionally substituted by fluorine, chlorine, hydroxyl, alkoxy, oxo or phenyl;

alkylaminocarbonyl or dialkylaminocarbonyl which is optionally substituted by fluorine, chlorine, hydroxyl, alkoxy, oxo or phenyl;

alkenylaminocarbonyl or dialkenylaminocarbonyl which is optionally substituted by fluorine, chlorine, hydroxyl, alkoxy, oxo or phenyl;

alkylsulfonyl which is optionally substituted by fluorine, chlorine, hydroxyl, alkoxy, alkylthio, oxo or phenyl;

alkenylsulfonyl which is optionally substituted by fluorine, chlorine, hydroxyl, alkoxy, oxo or phenyl;

or aryl, arylcarbonyl, aryl(thiocarbonyl), (arylthio)carbonyl, (arylthio)thiocarbonyl, aryloxycarbonyl, (arylamino)thiocarbonyl, arylsulfonyl, arylalkyl, arylalkenyl, arylalkynyl, arylalkylcarbonyl, arylalkenylcarbonyl or arylalkoxycarbonyl which is substituted by up to five radicals $R^7$ which are independent of each other, where $R^7$ is defined as above;

or heteroaryl, heteroarylalkyl, heteroarylalkenyl, heteroarylalkylcarbonyl or heteroarylalkenylcarbonyl which is substituted by up to three radicals $R^7$ which are independent of each other;

$R^5$ and $R^6$ are identical or different and are, independently of each other, hydrogen, carboxyl, alkyl which is optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl or alkoxycarbonyl;

alkenyl which is optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

alkynyl which is optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

cycloalkyl which is optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

cycloalkenyl which is optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

(cycloalkyl)-(alkyl) which is optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

(cycloalkenyl)-(alkyl) which is optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

alkylcarbonyl which is optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

alkenylcarbonyl which is optionally substituted by fluorine, chlorine or hydroxyl, alkoxy, oxo or phenyl;

(cycloalkyl)carbonyl which is optionally substituted by fluorine, chlorine or hydroxyl, alkoxy, oxo or phenyl;

(cycloalkenyl)carbonyl which is optionally substituted by fluorine, chlorine or hydroxyl, alkoxy, oxo or phenyl;

(cycloalkyl)-(alkyl)carbonyl which is optionally substituted by fluorine, chlorine or hydroxyl, alkoxy, oxo or phenyl;

(cycloalkenyl)-(alkyl)carbonyl which is optionally substituted by fluorine, chlorine or hydroxyl, alkoxy, oxo or phenyl;

alkyloxycarbonyl which is optionally substituted by fluorine, chlorine, bromine, hydroxyl, alkoxy, alkylamino, dialkylamino or alkylthio;

alkenyloxycarbonyl which is optionally substituted by fluorine, chlorine, hydroxyl, alkoxy, oxo or phenyl;

alkynyloxycarbonyl which is optionally substituted by fluorine, chlorine, hydroxyl, alkoxy, oxo or phenyl;

alkylthiocarbonyl which is optionally substituted by fluorine, chlorine, hydroxyl, alkoxy, oxo or phenyl;

alkenylthiocarbonyl which is optionally substituted by fluorine, chlorine, hydroxyl, alkoxy, oxo or phenyl;

alkylaminocarbonyl or dialkylaminocarbonyl which is optionally substituted by fluorine, chlorine, hydroxyl, alkoxy, oxo or phenyl;

alkenylaminocarbonyl or dialkenylaminocarbonyl which is optionally substituted by fluorine, chlorine, hydroxyl, alkoxy, oxo or phenyl;

alkylsulfonyl which is optionally substituted by fluorine, chlorine, hydroxyl, alkoxy, alkylthio, oxo or phenyl;

alkenylsulfonyl which is optionally substituted by fluorine, chlorine, hydroxyl, alkoxy, oxo or phenyl;

or aryl, arylcarbonyl, aryl(thiocarbonyl), (arylthio)carbonyl, (arylthio)thiocarbonyl, aryloxycarbonyl, (arylamino) thiocarbonyl, arylsulfonyl, arylalkyl, arylalkenyl, arylalkynyl, arylalkylcarbonyl, arylalkenylcarbonyl or arylalkoxycarbonyl which is substituted by up to five radicals $R^7$ which are independent of each other, where $R^7$ is defined as above;

or heteroaryl, heteroarylalkyl, heteroarylalkenyl, heteroarylalkylcarbonyl or heteroarylalkenylcarbonyl which is substituted by up to three radicals $R^7$ which are independent of each other, $R^5$ and $R^6$ can also together be a carbocycle which is of a ring size of $C_3$–$C_8$ and which is linked to the quinoline system via the double bond, and $R^3$ and $R^4$ are identical or different and are, independently of each other, hydrogen, alkyl which is optionally substituted by fluorine, chlorine, hydroxyl, amino, mercapto, acyloxy, benzoyloxy, benzyloxy, phenoxy, alkoxy, alkylamino, dialkylamino, alkylthio, alkylsulfonyl, alkylsulfinyl, carboxyl or carbamoyl;

alkenyl which is optionally substituted by fluorine, chlorine, hydroxyl, amino, mercapto, acyloxy, benzoyloxy, benzyloxy, phenoxy, alkoxy, alkylamino, dialkylamino, alkylthio, alkylsulfonyl, alkylsulfinyl, carboxyl or carbamoyl;

cycloalkyl which is optionally substituted by fluorine, chlorine, hydroxyl, amino, mercapto, acyloxy, benzoyloxy, benzyloxy, phenoxy, alkoxy, alkylamino, dialkylamino, alkylthio, alkylsulfonyl, alkylsulfinyl, carboxyl or carbamoyl;

cycloalkenyl which is optionally substituted by fluorine, chlorine, hydroxyl, amino, mercapto, acyloxy, benzoyloxy, benzyloxy, phenoxy, alkoxy, alkylamino, dialkylamino, alkylthio, alkylsulfonyl, alkylsulfinyl, carboxyl or carbamoyl;

or aryl, arylalkyl, heteroaryl or heteroarylalkyl which is substituted by up to five radicals $R^7$ which are independent of each other, where $R^7$ is defined as above, $R^3$ and $R^4$ can also together be a carbocycle which is of a ring size of $C_3$–$C_8$ and which is linked to the quinoline system in a spiro manner;

$R^3$ and $R^4$ can also together be a radical =C—$Z^1Z^2$ which is linked via a double bond and where $Z^1$ and $Z^2$ have the meaning given above for $R^3$ and $R^4$, their optical isomers and diastereomers in pure form or in the form of their mixtures, and their addition salts and prodrugs, with the exception of the compounds of the formula I in which $R^1$, $R^2$, $R^5$ and $R^6$ are hydrogen, $R^3$ and $R^4$ are methyl or are together a cyclopentyl ring which is linked in a spiro manner, and X is oxygen.

In a preferred group of compounds of the formula I and Ia:

2)

n is zero, one, two or three, the individual substituents $R^1$ are, independently of each other, fluorine, chlorine, bromine, iodine, trifluoromethyl, trifluoromethoxy, hydroxyl, $C_1$–$C_8$-alkyl, $C_5$–$C_8$-cycloalkyl, $C_1$–$C_8$-alkoxy, ($C_1$–$C_6$-alkoxy)-($C_1$–$C_4$-alkoxy), $C_1$–$C_6$-alkylthio, $C_1$–$C_6$-alkylsulfinyl, $C_1$–$C_6$-alkylsulfonyl, nitro, amino, azido, $C_1$–$C_6$-alkylamino, di($C_1$–$C_6$-alkyl)amino, piperidino, morpholino, 1-pyrrolidinyl, $C_1$–$C_6$-acyl, $C_1$–$C_6$-acyloxy, $C_1$–$C_6$-acylamino, cyano, carbamoyl, carboxyl, ($C_1$–$C_6$-alkyl)-oxycarbonyl, hydroxysulfonyl or sulfamoyl, or a phenyl, phenoxy, phenoxycarbonyl, phenylthio, phenylsulfinyl, phenylsulfonyl, phenoxysulfonyl, phenylsulfonyloxy, phenylsulfonylamino, benzoyl, heteroaryl or heteroarylmethyl radical which is optionally substituted by up to three radicals $R^7$ which are independent of each other, where $R^7$ can be fluorine, chlorine, bromine, iodine, cyano, trifluoromethyl, trifluoromethoxy, nitro, amino, azido, $C_1$–$C_6$-alkyl, $C_3$–$C_8$-cycloalkyl, $C_1$–$C_6$-alkoxy, $C_1$–$C_6$-alkylthio, $C_1$–$C_6$-alkylsulfinyl, $C_1$–$C_6$-alkylsulfonyl, $C_1$–$C_6$-alkylamino, di($C_1$–$C_6$-alkyl)amino, ($C_1$–$C_6$-alkyl)-oxycarbonyl, phenyl, phenoxy or heteroaryl, X is oxygen, sulfur, selenium or substituted nitrogen N—$R^2$ or N—O—$R^2$, where $R^2$ is hydrogen, alkyl which is optionally substituted by fluorine, chlorine, bromine, cyano, amino, mercapto, hydroxyl, acyloxy, benzoyloxy, benzyloxy, phenoxy, alkoxy, dialkylamino, alkylthio, alkylsulfonyl, phenylsulfonyl, oxo, thioxo, carboxyl or carbamoyl;

alkenyl which is optionally substituted by fluorine, chlorine, bromine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

alkynyl which is optionally substituted by fluorine, chlorine, bromine, mercapto, hydroxyl, acyloxy, benzoyloxy, benzyloxy, phenoxy, alkoxy, alkylamino or dialkylamino;

cycloalkyl which is optionally substituted by fluorine, chlorine, bromine, cyano, amino, mercapto, hydroxyl, acyloxy, benzoyloxy, benzyloxy, phenoxy, alkoxy, alkylamino or dialkylamino;

cycloalkenyl which is optionally substituted by fluorine, chlorine, bromine, cyano, amino, mercapto, hydroxyl, acyloxy, benzoyloxy, benzyloxy, phenoxy, alkoxy, alkylamino or dialkylamino;

(cycloalkyl)-(alkyl) which is optionally substituted by fluorine, chlorine, bromine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

(cycloalkenyl)-(alkyl) which is optionally substituted by fluorine, chlorine, bromine, cyano, amino, mercapto, hydroxyl, acyloxy, benzoyloxy, benzyloxy, phenoxy, alkoxy, alkylthio, alkylsulfonyl or phenylsulfonyl;

alkylcarbonyl which is optionally substituted by fluorine, chlorine, bromine, cyano, amino, mercapto, hydroxyl, acyloxy, benzoyloxy, benzyloxy, phenoxy or alkoxy;

alkenylcarbonyl which is optionally substituted by fluorine, chlorine or hydroxyl, alkoxy, oxo or phenyl;

(cycloalkyl)carbonyl which is optionally substituted by fluorine, chlorine or hydroxyl or alkoxy;

(cycloalkenyl)carbonyl which is optionally substituted by fluorine, chlorine or hydroxyl or alkoxy;

(cycloalkyl)-(alkyl)carbonyl;

(cycloalkenyl)-(alkyl)carbonyl;

alkyloxycarbonyl which is optionally substituted by fluorine, chlorine, bromine, hydroxyl, alkoxy, alkylamino, dialkylamino or alkylthio;

alkenyloxycarbonyl;

alkynyloxycarbonyl;

alkylthiocarbonyl which is optionally substituted by fluorine, chlorine, alkoxy, oxo or phenyl;

alkenylthiocarbonyl which is optionally substituted by fluorine, chlorine, alkoxy, oxo or phenyl;

alkylaminocarbonyl or dialkylaminocarbonyl;

alkenylaminocarbonyl or dialkenylaminocarbonyl which is optionally substituted by fluorine, chlorine, hydroxyl, alkoxy, oxo or phenyl;

alkylsulfonyl which is optionally substituted by fluorine, chlorine, hydroxyl, alkoxy, oxo or phenyl;

alkenylsulfonyl;

or aryl, arylcarbonyl, aryl(thiocarbonyl), (arylthio)carbonyl, (arylthio)thiocarbonyl, aryloxycarbonyl, (arylamino)thiocarbonyl, arylsulfonyl, arylalkyl, arylalkenyl, arylalkynyl, arylalkylcarbonyl, arylalkenylcarbonyl or arylalkoxycarbonyl which is substituted by up to 2 radicals $R^7$ which are independent of each other, where $R^7$ is defined as above;

or heteroaryl, heteroarylalkyl, heteroarylalkenyl, heteroarylalkylcarbonyl or heteroarylalkenylcarbonyl which is substituted by up to three radicals $R^7$ which are independent of each other;

$R^5$ and $R^6$ are identical or different and are, independently of each other, hydrogen, $C_1-C_8$-alkyl which is optionally substituted by fluorine, chlorine, bromine, iodine, cyano, amino, mercapto, hydroxyl, $C_1-C_6$-acyloxy, benzoyloxy, benzyloxy, phenoxy, $C_1-C_6$-alkoxy, $C_1-C_6$-alkylamino, di($C_1-C_6$-alkyl)amino, $C_1-C_6$-alkylthio, $C_1-C_6$-alkylsulfonyl, phenylsulfonyl, oxo, thioxo, carboxyl or carbamoyl;

$C_2-C_8$-alkenyl which is optionally substituted by fluorine, chlorine, bromine, iodine, cyano, amino, mercapto, hydroxyl, $C_1-C_6$-acyloxy, benzoyloxy, benzyloxy, phenoxy, $C_1-C_6$-alkoxy, $C_1-C_6$-alkylamino, di($C_1-C_6$-alkyl)amino, $C_1-C_6$-alkylthio, $C_1-C_6$-alkylsulfonyl, phenylsulfonyl, oxo, thioxo, carboxyl or carbamoyl;

$C_3-C_8$-alkynyl which is optionally substituted by fluorine, chlorine, bromine, iodine, cyano, amino, mercapto, hydroxyl, $C_1-C_6$-acyloxy, benzoyloxy, benzyloxy, phenoxy, $C_1-C_6$-alkoxy, $C_1-C_6$-alkylamino, di($C_1-C_6$-alkyl)amino, $C_1-C_6$-alkylthio, $C_1-C_6$-alkylsulfonyl, phenylsulfonyl, oxo, thioxo, carboxyl or carbamoyl;

$C_3-C_8$-cycloalkyl which is optionally substituted by fluorine, chlorine, bromine, iodine, cyano, amino, mercapto, hydroxyl, $C_1-C_6$-acyloxy, benzoyloxy, benzyloxy, phenoxy, $C_1-C_6$-alkoxy, $C_1-C_6$-alkylamino, di($C_1-C_6$-alkyl)amino, $C_1-C_6$-alkylthio, $C_1-C_6$-alkylsulfonyl, phenylsulfonyl, oxo, thioxo, carboxyl or carbamoyl;

$C_5-C_8$-cycloalkenyl which is optionally substituted by fluorine, chlorine, bromine, iodine, cyano, amino, mercapto, hydroxyl, $C_1-C_6$-acyloxy, benzoyloxy, benzyloxy, phenoxy, $C_1-C_6$-alkoxy, $C_1-C_6$-alkylamino, di($C_1-C_6$-alkyl)amino, $C_1-C_6$-alkylthio, $C_1-C_6$-alkylsulfonyl, phenylsulfonyl, oxo, thioxo, carboxyl or carbamoyl;

($C_3-C_8$-cycloalkyl)-($C_1-C_4$-alkyl) which is optionally substituted by fluorine, chlorine, bromine, iodine, cyano, amino, mercapto, hydroxyl, $C_1-C_6$-acyloxy, benzoyloxy, benzyloxy, phenoxy, $C_1-C_6$-alkoxy, $C_1-C_6$-alkylamino, di($C_1-C_6$-alkyl)amino, $C_1-C_6$-alkylthio, $C_1-C_6$-alkylsulfonyl, phenylsulfonyl, oxo, thioxo, carboxyl or carbamoyl;

($C_5-C_8$-cycloalkenyl)-($C_1-C_4$-alkyl) which is optionally substituted by fluorine, chlorine, bromine, iodine, cyano, amino, mercapto, hydroxyl, $C_1-C_6$-acyloxy, benzoyloxy, benzyloxy, phenoxy, $C_1-C_6$-alkoxy, $C_1-C_6$-alkylamino, di($C_1-C_6$-alkyl)amino, $C_1-C_6$-alkylthio, $C_1-C_6$-alkylsulfonyl, phenylsulfonyl, oxo, thioxo, carboxyl or carbamoyl;

$C_1-C_6$-alkylcarbonyl which is optionally substituted by fluorine, chlorine, bromine, iodine, cyano, amino, mercapto, hydroxyl, $C_1-C_6$-acyloxy, benzoyloxy, benzyloxy, phenoxy, $C_1-C_6$-alkoxy, $C_1-C_6$-alkylamino, di($C_1-C_6$-alkyl)amino, $C_1-C_6$-alkylthio, $C_1-C_6$-alkylsulfonyl, phenylsulfonyl, oxo, thioxo, carboxyl or carbamoyl;

$C_2-C_8$-alkenylcarbonyl which is optionally substituted by fluorine, chlorine or hydroxyl, $C_1-C_4$-alkoxy, oxo or phenyl;

($C_3-C_8$-cycloalkyl)carbonyl which is optionally substituted by fluorine, chlorine or hydroxyl, $C_1-C_4$-alkoxy, oxo or phenyl;

($C_5-C_8$-cycloalkenyl)carbonyl which is optionally substituted by fluorine, chlorine or hydroxyl, $C_1-C_4$-alkoxy, oxo or phenyl;

($C_3-C_8$cycloalkyl)-($C_1-C_3$-alkyl)carbonyl which is optionally substituted by fluorine, chlorine or hydroxyl, $C_1-C_4$-alkoxy, oxo or phenyl;

($C_5-C_6$-cycloalkenyl)-($C_1-C_3$-alkyl)carbonyl which is optionally substituted by fluorine, chlorine or hydroxyl, $C_1-C_4$-alkoxy, oxo or phenyl;

$C_1-C_8$-alkyloxycarbonyl which is optionally substituted by fluorine, chlorine, bromine, hydroxyl, $C_1-C_4$-alkoxy, $C_1-C_4$-alkylamino, di($C_1-C_4$-alkyl)amino or $C_1-C_4$-alkylthio;

$C_2-C_8$-alkenyloxycarbonyl which is optionally substituted by fluorine, chlorine, hydroxyl, $C_1-C_4$-alkoxy, oxo or phenyl;

$C_2-C_8$-alkynyloxycarbonyl which is optionally substituted by fluorine, chlorine, hydroxyl, $C_1-C_4$-alkoxy, oxo or phenyl;

$C_1-C_8$-alkylthiocarbonyl which is optionally substituted by fluorine, chlorine, hydroxyl, $C_1-C_4$-alkoxy, oxo or phenyl;

$C_2-C_8$-alkenylthiocarbonyl which is optionally substituted by fluorine, chlorine, hydroxyl, $C_1-C_4$-alkoxy, oxo or phenyl;

$C_1-C_8$-alkylaminocarbonyl or di($C_1-C_8$-alkyl)aminocarbonyl which is optionally substituted by fluorine, chlorine, hydroxyl, $C_1-C_4$-alkoxy, oxo or phenyl;

$C_2-C_8$-alkenylaminocarbonyl or di($C_2-C_6$-alkenyl)aminocarbonyl which is optionally substituted by fluorine, chlorine, hydroxyl, $C_1-C_4$-alkoxy, oxo or phenyl;

$C_1-C_6$-alkylsulfonyl which is optionally substituted by fluorine, chlorine, hydroxyl, $C_1-C_4$-alkoxy, $C_1-C_4$-alkylthio, oxo or phenyl;

$C_2-C_6$-alkenylsulfonyl which is optionally substituted by fluorine, chlorine, hydroxyl, $C_1-C_4$-alkoxy, oxo or phenyl;

or aryl, arylcarbonyl, aryl(thiocarbonyl), (arylthio)carbonyl, (arylthio)thiocarbonyl, aryloxycarbonyl, (arylamino)

thiocarbonyl, arylsulfonyl, arylalkyl, arylalkenyl, arylalkynyl, arylalkylcarbonyl, arylalkenylcarbonyl or arylalkoxycarbonyl which is substituted by up to three radicals $R^7$ which are independent of each other, where the alkyl radical can in each case contain from 1 to 5 carbon atoms and $R^7$ is defined as above;

or heteroaryl, heteroarylalkyl, heteroarylalkenyl, heteroarylalkylcarbonyl or heteroarylalkenylcarbonyl which is substituted by up to three radicals $R^7$ which are independent of each other, where the alkyl radical can in each case contain from 1 to 3 carbon atoms;

$R^5$ and $R^6$ can also together be a carbocycle which is of a ring size of $C_3$–$C_8$ and which is linked to the quinoline system via the double bond, and $R^3$ and $R^4$ are identical or different and are, independently of each other, hydrogen, $C_1$–$C_8$-alkyl which is optionally substituted by fluorine, chlorine, hydroxyl, amino, mercapto, $C_1$–$C_4$-acyloxy, benzoyloxy, benzyloxy, phenoxy, $C_1$–$C_4$-alkoxy, $C_1$–$C_4$-alkylamino, di($C_1$–$C_4$-alkyl)amino, $C_1$–$C_4$-alkylthio, $C_1$–$C_4$-alkylsulfonyl, $C_1$–$C_4$-alkylsulfinyl, carboxyl or carbamoyl;

$C_2$–$C_8$-alkenyl which is optionally substituted by fluorine or chlorine, hydroxyl, amino, mercapto, $C_1$–$C_4$-acyloxy, benzoyloxy, benzyloxy, phenoxy, $C_1$–$C_4$-alkoxy, $C_1$–$C_4$-alkylamino, di($C_1$–$C_4$-alkyl)amino, $C_1$–$C_4$-alkylthio, $C_1$–$C_4$-alkylsulfonyl, $C_1$–$C_4$-alkylsulfinyl, carboxyl or carbamoyl;

$C_3$–$C_8$-cycloalkyl which is optionally substituted by fluorine or chlorine, hydroxyl, amino, mercapto, $C_1$–$C_4$-acyloxy, benzoyloxy, benzyloxy, phenoxy, $C_1$–$C_4$-alkoxy, $C_1$–$C_4$-alkylamino, di($C_1$–$C_4$-alkyl)amino, $C_1$–$C_4$-alkylthio, $C_1$–$C_4$-alkylsulfonyl, $C_1$–$C_4$-alkylsulfinyl, carboxyl or carbamoyl;

$C_3$–$C_8$-cycloalkenyl which is optionally substituted by fluorine or chlorine, hydroxyl, amino, mercapto, $C_1$–$C_4$-acyloxy, benzoyloxy, benzyloxy, phenoxy, $C_1$–$C_4$-alkoxy, $C_1$–$C_4$-alkylamino, di($C_1$–$C_4$-alkyl)amino, $C_1$–$C_4$-alkylthio, $C_1$–$C_4$-alkylsulfonyl, $C_1$–$C_4$-alkylsulfinyl, carboxyl or carbamoyl;

aryl, arylalkyl, heteroaryl or heteroarylalkyl which is substituted by up to three radicals $R^7$ which are independent of each other, where the alkyl radical can in each case contain from 1 to 3 carbon atoms and $R^7$ is defined as above;

$R^3$ and $R^4$ can also, in structures of the formulae I and Ia, together be a carbocycle which is of a ring size of $C_3$–$C_8$ and which is linked to the quinoline system in a spiro manner;

in addition, $R^3$ and $R^4$ can together be a radical =C—$Z^1Z^2$ which is linked via a double bond and where $Z^1$ and $Z^2$ have the meaning given above for $R^3$ and $R^4$.

In a group of compounds of the formula I and Ia which is yet again preferred:

3)

n is zero, one or two, the individual substituents $R^1$ are, independently of each other, fluorine, chlorine, bromine, trifluoromethyl, trifluoromethoxy, hydroxyl, $C_1$–$C_6$-alkyl, $C_5$–$C_6$-cycloalkyl, $C_1$–$C_6$-alkoxy, ($C_1$–$C_6$-alkoxy)-($C_1$–$C_2$-alkoxy), $C_1$–$C_4$-alkylthio, $C_1$–$C_4$-alkylsulfinyl, $C_1$–$C_4$-alkylsulfonyl, nitro, amino, $C_1$–$C_4$-alkylamino, di($C_1$–$C_4$-alkyl)amino, $C_1$–$C_6$-acyl, $C_1$–$C_4$-acyloxy, $C_1$–$C_4$-acylamino, cyano, carbamoyl, carboxyl or ($C_1$–$C_4$-alkyl)-oxycarbonyl, or a phenyl, phenoxy, phenoxycarbonyl, phenylthio, phenylsulfinyl, phenylsulfonyl, phenoxysulfonyl, phenylsulfonyloxy, phenylsulfonylamino, benzoyl, heteroaryl or heteroarylmethyl radical which is optionally substituted by up to two radicals $R^7$ which are independent of each other, where $R^7$ can be fluorine, chlorine, trifluoromethyl, trifluoromethoxy, nitro, amino, $C_1$–$C_4$-alkyl, $C_3$–$C_6$-cycloalkyl, $C_1$–$C_4$-alkoxy, $C_1$–$C_4$-alkylthio, $C_1$–$C_4$-alkylsulfinyl, $C_1$–$C_4$-alkylsulfonyl, $C_1$–$C_4$-alkylamino, di($C_1$–$C_4$-alkyl)amino, phenyl, phenoxy or heteroaryl.

X is oxygen, sulfur or substituted nitrogen N—$R^2$ or N—O—$R^2$.

where $R^2$ is hydrogen, alkyl which is optionally substituted by fluorine, chlorine, cyano, amino, mercapto, hydroxyl, acyloxy, benzoyloxy, benzyloxy, phenoxy, alkoxy, dialkylamino, alkylthio, alkylsulfonyl, phenylsulfonyl, oxo, thioxo or carboxyl;

alkenyl which is optionally substituted by fluorine, chlorine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo or carboxyl;

alkynyl;

cycloalkyl;

cycloalkenyl;

(cycloalkyl)-(alkyl) which is optionally substituted by fluorine, chlorine, bromine, amino, mercapto, hydroxyl, acyloxy, benzoyloxy, benzyloxy, phenoxy, alkoxy, alkylamino, dialkylamino, alkylthio, alkylsulfonyl or phenylsulfonyl;

(cycloalkenyl)-(alkyl);

alkylcarbonyl which is optionally substituted by fluorine, chlorine, hydroxyl, alkoxy or oxo;

alkenylcarbonyl;

(cycloalkyl)carbonyl;

(cycloalkenyl)carbonyl;

alkyloxycarbonyl which is optionally substituted by fluorine, chlorine, bromine, hydroxyl or alkoxy;

alkenyloxycarbonyl;

alkylthiocarbonyl;

alkylaminocarbonyl or dialkylaminocarbonyl;

alkenylaminocarbonyl or dialkenylaminocarbonyl;

alkylsulfonyl;

or aryl, arylcarbonyl, aryl(thiocarbonyl), (arylthio)carbonyl, (arylthio)thiocarbonyl, aryloxycarbonyl, arylsulfonyl, arylalkyl, arylalkenyl, arylalkylcarbonyl, arylalkenylcarbonyl or arylalkoxycarbonyl which is substituted by up to 2 radicals $R^7$ which are independent of each other, where $R^7$ is defined as above;

or heteroaryl, heteroarylalkyl, heteroarylalkenyl, heteroarylalkylcarbonyl, or heteroarylalkenylcarbonyl which is substituted by up to two radicals $R^7$ which are independent of each other;

$R^5$ and $R^6$ are identical or different and are, independently of each other, hydrogen, $C_1$–$C_6$-alkyl which is optionally substituted by fluorine, chlorine, bromine, iodine, cyano, amino, mercapto, hydroxyl, $C_1$–$C_4$-acyloxy, benzoyloxy, benzyloxy, phenoxy, $C_1$–$C_4$-alkoxy, $C_1$–$C_4$-alkylamino, di($C_1$–$C_4$-alkyl)amino, $C_1$–$C_4$-alkylthio, $C_1$–$C_4$-alkylsulfonyl, phenylsulfonyl, oxo, thioxo, carboxyl or carbamoyl;

$C_2$–$C_6$-alkenyl which is optionally substituted by fluorine, chlorine, cyano, amino, mercapto, hydroxyl, $C_1$–$C_4$-acyloxy, benzoyloxy, benzyloxy, phenoxy, $C_1$–$C_4$-alkoxy, $C_1$–$C_4$-alkylamino, di($C_1$–$C_4$-alkyl)amino, $C_1$–$C_4$-alkylthio, $C_1$–$C_4$-alkylsulfonyl, phenylsulfonyl, carboxyl or carbamoyl;

$C_3$–$C_6$-alkynyl which is optionally substituted by fluorine, chlorine, cyano, amino, mercapto, hydroxyl, $C_1$–$C_4$-acyloxy, benzoyloxy, benzyloxy, phenoxy, $C_1$–$C_4$-alkoxy, $C_1$–$C_4$-alkylamino, di($C_1$–$C_4$-alkyl)amino, $C_1$–$C_4$-alkylthio, $C_1$–$C_4$-alkylsulfonyl, phenylsulfonyl, carboxyl or carbamoyl;

$C_3$–$C_6$-cycloalkyl which is optionally substituted by fluorine, chlorine, cyano, amino, mercapto, hydroxyl, $C_1$–$C_4$-acyloxy, benzoyloxy, benzyloxy, phenoxy, $C_1$–$C_4$-alkoxy, $C_1$–$C_4$-alkylamino, di($C_1$–$C_4$-alkyl)amino, $C_1$–$C_4$-alkylthio, $C_1$–$C_4$-alkylsulfonyl, phenylsulfonyl, carboxyl or carbamoyl;

$C_5$–$C_6$-cycloalkenyl which is optionally substituted by fluorine, chlorine, cyano, mercapto, hydroxyl, $C_1$–$C_4$-acyloxy, benzoyloxy, benzyloxy, phenoxy, $C_1$–$C_4$-alkoxy, $C_1$–$C_4$-alkylthio, $C_1$–$C_4$-alkylsulfonyl, phenylsulfonyl, carboxyl or carbamoyl;

($C_3$–$C_6$-cycloalkyl)-($C_1$–$C_2$-alkyl) which is optionally substituted by fluorine, chlorine, cyano, amino, mercapto, hydroxyl, $C_1$–$C_4$-acyloxy, benzoyloxy, benzyloxy, phenoxy, $C_1$–$C_4$-alkoxy, $C_1$–$C_4$-alkylthio or carboxyl;

($C_5$–$C_6$-cycloalkenyl)-($C_1$–$C_2$-alkyl) which is optionally substituted by fluorine, chlorine, cyano, amino, mercapto, hydroxyl, $C_1$–$C_4$-acyloxy, benzoyloxy, benzyloxy, phenoxy, $C_1$–$C_4$-alkoxy, $C_1$–$C_4$-alkylthio or carboxyl;

$C_1$–$C_6$-alkylcarbonyl which is optionally substituted by fluorine, chlorine, cyano, amino, mercapto, hydroxyl, $C_1$–$C_4$-acyloxy, benzoyloxy, benzyloxy, phenoxy, $C_1$–$C_4$-alkoxy, $C_1$–$C_4$-alkylamino, di($C_1$–$C_4$-alkyl)amino, $C_1$–$C_4$-alkylthio, $C_1$–$C_4$-alkylsulfonyl, phenylsulfonyl, carboxyl or carbamoyl;

$C_2$–$C_6$-alkenylcarbonyl which is optionally substituted by fluorine, chlorine, hydroxyl, $C_1$–$C_4$-alkoxy, oxo or phenyl;

($C_3$–$C_6$-cycloalkyl)carbonyl which is optionally substituted by fluorine, chlorine, hydroxyl, $C_1$–$C_4$-alkoxy, oxo or phenyl;

($C_5$–$C_6$-cycloalkenyl)carbonyl;

($C_3$–$C_6$-cycloalkyl)-($C_1$–$C_2$-alkyl)carbonyl which is optionally substituted by fluorine, chlorine, hydroxyl, $C_1$–$C_4$-alkoxy, oxo or phenyl;

($C_5$–$C_6$-cycloalkenyl)-($C_3$–$C_2$-alkyl)carbonyl;

$C_1$–$C_6$-alkyloxycarbonyl which is optionally substituted by fluorine, chlorine, $C_1$–$C_4$-alkoxy, $C_1$–$C_4$-alkylamino, di($C_1$–$C_4$-alkyl)amino or $C_1$–$C_4$-alkylthio;

$C_2$–$C_6$-alkenyloxycarbonyl which is optionally substituted by fluorine, chlorine, $C_1$–$C_4$-alkoxy or phenyl; $C_2$–$C_6$-alkynyloxycarbonyl;

$C_1$–$C_6$-alkylthiocarbonyl which is optionally substituted by fluorine, chlorine, $C_1$–$C_4$-alkoxy or phenyl;

$C_2$–$C_6$-alkenylthiocarbonyl which is optionally substituted by fluorine, chlorine, $C_1$–$C_4$-alkoxy or phenyl;

$C_1$–$C_6$-alkylaminocarbonyl or di($C_1$–$C_6$-alkyl)aminocarbonyl which is optionally substituted by fluorine, chlorine, $C_1$–$C_4$-alkoxy or phenyl;

$C_2$–$C_6$-alkenylaminocarbonyl or di($C_2$–$C_6$-alkenyl)aminocarbonyl;

$C_1$–$C_6$-alkylsulfonyl which is optionally substituted by fluorine, chlorine, $C_1$–$C_4$-alkoxy or phenyl;

$C_2$–$C_6$-alkenylsulfonyl;

or aryl, arylcarbonyl, aryl(thiocarbonyl), (arylthio)carbonyl, (arylthio)thiocarbonyl, aryloxycarbonyl, (arylamino)thiocarbonyl, arylsulfonyl, arylalkyl, arylalkenyl, arylalkynyl, arylalkylcarbonyl, arylalkenylcarbonyl or arylalkoxycarbonyl which is substituted by up to three radicals $R^7$ which are independent of each other, where the alkyl radical can in each case contain from 1 to 4 carbon atoms and $R^7$ is defined as above;

or heteroaryl, heteroarylalkyl, heteroarylalkenyl, heteroarylalkylcarbonyl or heteroarylalkenylcarbonyl which is substituted by up to three radicals $R^7$ which are independent of each other, where the alkyl radical can in each case contain from 1 to 3 carbon atoms, and $R^5$ and $R^6$ can also together be a carbocycle which is of a ring size of $C_5$–$C_6$ and which is linked to the quinoline system via the double bond.

$R^3$ and $R^4$ are identical or different and are, independently of each other, $C_1$–$C_6$-alkyl which is optionally substituted by fluorine, chlorine, hydroxyl, amino, mercapto, $C_1$–$C_4$-acyloxy, benzoyloxy, benzyloxy, phenoxy, $C_1$–$C_4$-alkoxy, $C_1$–$C_4$-alkylamino, di($C_1$–$C_4$-alkyl)amino, $C_1$–$C_4$-alkylthio, $C_1$–$C_4$-alkylsulfonyl, $C_1$–$C_4$-alkylsulfinyl, carboxyl or carbamoyl;

$C_2$–$C_6$-alkenyl which is optionally substituted by fluorine or chlorine, phenoxy, $C_1$–$C_4$-alkoxy, $C_1$–$C_4$-alkylthio, $C_1$–$C_4$-alkylsulfonyl or $C_1$–$C_4$-alkylsulfinyl;

$C_3$–$C_6$-cycloalkyl which is optionally substituted by fluorine, chlorine, hydroxyl, amino, mercapto, $C_1$–$C_4$-acyloxy, benzoyloxy, benzyloxy, phenoxy, $C_1$–$C_4$-alkoxy, $C_1$–$C_4$-alkylamino, di($C_1$–$C_4$-alkyl)amino, $C_1$–$C_4$-alkylthio, $C_1$–$C_4$-alkylsulfonyl or $C_1$–$C_4$-alkylsulfinyl;

$C_3$–$C_6$-cycloalkenyl which is optionally substituted by fluorine or chlorine, phenoxy, $C_1$–$C_4$-alkoxy, $C_1$–$C_4$-alkylthio, $C_1$–$C_4$-alkylsulfonyl or $C_1$–$C_4$-alkylsulfinyl;

aryl, arylalkyl, heteroaryl or heteroarylalkyl which is substituted by up to three radicals $R^7$ which are independent of each other, where the alkyl radical can in each case contain from 1 to 3 carbon atoms and $R^7$ is defined as above, it being possible for one of the radicals $R^3$ or $R^4$ to be hydrogen.

$R^3$ and $R^4$ can also, in structures of the formulae I and Ia, together be a carbocycle which is of a ring size of $C_4$–$C_6$ and which is linked to the quinoline system in a spiro manner;

in addition, $R^3$ and $R^4$ can together also be a radical =C—$Z^1Z^2$ which is linked via a double bond and where $Z^1$ and $Z^2$ have the meaning given above for $R^3$ and $R^4$.

In a group of compounds of the formula I and Ia which is yet again preferred:

4)

n is zero, one or two, the individual substituents $R^1$ are, independently of each other, fluorine, chlorine, trifluoromethyl, trifluoromethoxy, hydroxyl, $C_1$–$C_4$-alkyl, $C_1$–$C_4$-alkoxy, ($C_1$–$C_4$-alkoxy)-($C_1$–$C_2$-alkoxy), $C_1$–$C_4$-alkylthio, $C_1$–$C_4$-alkylsulfinyl, $C_1$–$C_4$-alkylsulfonyl, di($C_1$–$C_4$-alkyl)amino, $C_1$–$C_4$-acyl, $C_1$–$C_4$-acyloxy, carbamoyl, carboxyl or ($C_1$–$C_4$-alkyl)-oxycarbonyl, or a phenyl, phenoxy, phenoxycarbonyl, phenylthio, phenylsulfinyl, phenylsulfonyl, benzoyl, heteroaryl or heteroarylmethyl radical;

X is oxygen, sulfur or substituted nitrogen N—$R^2$ or N—O—$R^2$, where $R^2$ is hydrogen or ($C_1$–$C_4$)-alkyl;

($C_2$–$C_5$)-alkenyl;

($C_1$–$C_4$)-alkylcarbonyl;

($C_2$–$C_5$)-alkenylcarbonyl;

($C_1$–$C_4$)-alkyloxycarbonyl;

or aryl, arylcarbonyl, aryl(thiocarbonyl), (arylthio)carbonyl, (arylthio)thiocarbonyl, aryloxycarbonyl, arylsulfonyl, arylalkyl, arylalkylcarbonyl, arylalkenylcarbonyl or arylalkoxycarbonyl;

or heteroaryl or heteroarylalkyl;

$R^5$ and $R^6$ are identical or different and are, independently of each other, hydrogen, $C_1$–$C_6$-alkyl which is optionally substituted by fluorine, chlorine, amino, mercapto, hydroxyl, $C_1$–$C_4$-acyloxy, benzoyloxy, benzyloxy, phenoxy, $C_1$–$C_4$-alkoxy, $C_1$–$C_4$-alkylamino, di($C_1$–$C_4$-alkyl)amino or $C_1$–$C_4$-alkylthio;

$C_2$–$C_6$-alkenyl which is optionally substituted by fluorine, chlorine, amino, mercapto, hydroxyl, $C_1$–$C_4$-acyloxy, benzoyloxy, benzyloxy, phenoxy, $C_1$–$C_4$-alkoxy, $C_1$–$C_4$-alkylamino, di($C_1$–$C_4$-alkyl)amino or $C_1$–$C_4$-alkylthio;

$C_3$–$C_6$-cycloalkyl, $C_5$–$C_6$-cycloalkenyl, ($C_3$–$C_6$-cycloalkyl)-($C_1$–$C_2$-alkyl), ($C_5$–$C_6$-cycloalkenyl)-($C_1$–$C_2$-alkyl), $C_1$–$C_6$-alkylcarbonyl which is optionally substituted by fluorine, chlorine, $C_1$–$C_4$-acyloxy, benzoyloxy, benzyloxy, phenoxy, $C_1$–$C_4$-alkoxy, $C_1$–$C_4$-alkylamino, di($C_1$–$C_4$-alkyl)amino or $C_1$–$C_4$-alkylthio;

$C_2$–$C_4$-alkenylcarbonyl;

($C_3$–$C_6$-cycloalkyl)carbonyl;

($C_3$–$C_6$-cycloalkyl)-($C_1$–$C_2$-alkyl)carbonyl;

$C_1$–$C_6$-alkyloxycarbonyl which is optionally substituted by $C_1$–$C_4$-alkylamino, di($C_1$–$C_4$-alkyl)amino or $C_1$–$C_4$-alkylthio;

$C_1$–$C_6$-alkylthiocarbonyl;

di($C_1$–$C_6$-alkyl)aminocarbonyl;

di($C_2$–$C_4$-alkenyl)aminocarbonyl;

$C_1$–$C_6$-alkylsulfonyl;

or aryl, arylcarbonyl, aryl(thiocarbonyl), (arylthio)carbonyl, (arylthio)thiocarbonyl, aryloxycarbonyl, (arylamino)thiocarbonyl, arylsulfonyl, arylalkyl, arylalkenyl, arylalkynyl, arylalkylcarbonyl, arylalkenylcarbonyl or arylalkoxycarbonyl which is substituted by up to two radicals $R^7$ which are independent of each other, where the alkyl radical can in each case contain from 1 to 3 carbon atoms and $R^7$ is defined as above.

or heteroaryl, heteroarylalkyl, heteroarylalkenyl, heteroarylalkylcarbonyl or heteroarylalkenylcarbonyl which is substituted by up to two radicals $R^7$ which are independent of each other, where the alkyl radical can in each case contain from 1 to 2 carbon atoms, and $R^5$ and $R^6$ can also together be a carbocycle which is of a ring size of $C_5$–$C_6$ and which is linked to the quinoline system via the double bond, $R^3$ and $R^4$ are identical or different and are, independently of each other, $C_1$–$C_6$-alkyl which is optionally substituted by fluorine, chlorine, hydroxyl, amino, mercapto, $C_1$–$C_4$-acyloxy, benzoyloxy, benzyloxy, phenoxy, $C_1$–$C_4$-alkoxy, $C_1$–$C_4$-alkylamino, di($C_1$–$C_4$-alkyl)amino, $C_1$–$C_4$-alkylthio, $C_1$–$C_4$-alkylsulfonyl, $C_1$–$C_4$-alkyl-sulfinyl or carboxyl;

$C_2$–$C_6$-alkenyl which is optionally substituted by fluorine or chlorine;

$C_3$–$C_6$-cycloalkyl, $C_5$–$C_6$-cycloalkenyl which is optionally substituted by fluorine or chlorine;

with it also being possible for one of the radicals $R^3$ and $R^4$ to be hydrogen;

$R^3$ and $R^4$ can also, in structures of the formulae I and Ia, together be a carbocycle which is of a ring size of $C_4$–$C_6$ and which is linked to the quinoline system in a spiro manner, $R^3$ and $R^4$ can together also be a radical =C—$Z^1Z^2$ which is linked via a double bond and where $Z^1$ and $Z^2$ have the meaning given above for $R^3$ and $R^4$.

In a very particularly preferred group of compounds of the formula I and Ia:

5)

n is zero, one or two, the individual substituents $R^1$ are, independently of each other, fluorine, chlorine, trifluoromethoxy, hydroxyl, $C_1$–$C_4$-alkoxy or $C_1$–$C_4$-alkylthio, X is oxygen, sulfur or substituted nitrogen N—$R^2$ or N—O—$R^2$.

where $R^2$ is hydrogen;

$R^5$ and $R^6$ are identical or different and are, independently of each other, hydrogen, $C_1$–$C_6$-alkyl which is optionally substituted by fluorine, chlorine, amino, mercapto, hydroxyl, $C_1$–$C_4$-acyloxy, benzoyloxy, benzyloxy, phenoxy, $C_1$–$C_4$-alkoxy, $C_1$–$C_4$-alkylamino, di($C_1$–$C_4$-alkyl)amino or $C_1$–$C_4$-alkylthio;

$C_2$–$C_6$-alkenyl which is optionally substituted by fluorine, chlorine, amino, mercapto, hydroxyl, $C_1$–$C_4$-acyloxy, benzoyloxy, benzyloxy, phenoxy, $C_3$–$C_4$-alkoxy, $C_1$–$C_4$-alkylamino, di($C_1$–$C_4$-alkyl)amino or $C_1$–$C_4$-alkylthio;

where at least one substituent of $R^5$ and $R^6$ is hydrogen, and $R^5$ and $R^6$ can also together be a carbocycle which is of a ring size of $C_5$–$C_6$ and which is linked to the quinoline system via the double bond, $R^3$ and $R^4$ are identical or different and are, independently of each other, $C_1$–$C_2$-alkyl;

$R^3$ and $R^4$ can also, in structures of the formulae I and Ia, together be a carbocycle which is of a ring size of $C_4$–$C_6$ and which is linked to the quinoline system in a spiro manner.

The present invention also relates to 6) the use of compounds of the formula I, and also their tautomeric forms of the formula Ia, in which:

n is zero, one, two, three or four, the individual substituents $R^1$ are, independently of each other, fluorine, chlorine, bromine, iodine, trifluoromethyl, trifluoromethoxy, hydroxyl, alkyl, cycloalkyl, alkoxy, alkoxy(alkoxy), alkylthio, alkylsulfinyl, alkylsulfonyl, nitro, amino, azido, alkylamino, dialkylamino, piperidino, morpholino, 1-pyrrolidinyl, acyl, acyloxy, acylamino, cyano, carbamoyl, carboxyl, alkyloxycarbonyl, hydroxysulfonyl or sulfamoyl, or a phenyl, phenoxy, phenoxycarbonyl, phenylthio, phenylsulfinyl, phenylsulfonyl, phenoxysulfonyl, phenylsulfonyloxy, anilinosulfonyl, phenylsulfonylamino, benzoyl, heteroaroyl, heteroaryl, heteroarylmethyl, heteroarylmethyloxy or heteroarylmethylthio radical which is optionally substituted by up to five radicals $R^7$ which are independent of each other, where $R^7$ can be fluorine, chlorine, bromine, iodine, cyano, trifluoromethyl, trifluoromethoxy, nitro, amino, azido, alkyl, cycloalkyl, alkoxy, alkylthio, alkylsulfinyl, alkylsulfonyl, alkylamino, dialkylamino, alkyloxycarbonyl, phenyl, phenoxy or heteroaryl, X is oxygen, sulfur, selenium or substituted nitrogen N—R$^2$ or N—O—R$^2$, where R$^2$ is hydrogen;

alkyl which is optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl or alkoxycarbonyl;

alkenyl which is optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

alkynyl which is optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

cycloalkyl which is optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

cycloalkenyl which is optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

(cycloalkyl)-(alkyl) which is optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

(cycloalkenyl)-(alkyl) which is optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

alkylcarbonyl which is optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

alkenylcarbonyl which is optionally substituted by fluorine, chlorine or hydroxyl, alkoxy, oxo or phenyl;

(cycloalkyl)carbonyl which is optionally substituted by fluorine, chlorine or hydroxyl, alkoxy, oxo or phenyl;

(cycloalkenyl)carbonyl which is optionally substituted by fluorine, chlorine or hydroxyl, alkoxy, oxo or phenyl;

(cycloalkyl)-(alkyl)carbonyl which is optionally substituted by fluorine, chlorine or hydroxyl, alkoxy, oxo or phenyl;

(cycloalkenyl)-(alkyl)carbonyl which is optionally substituted by fluorine, chlorine or hydroxyl, alkoxy, oxo or phenyl;

alkyloxycarbonyl which is optionally substituted by fluorine, chlorine, bromine, hydroxyl, alkoxy, alkylamino, dialkylamino or alkylthio;

alkenyloxycarbonyl which is optionally substituted by fluorine, chlorine, hydroxyl, alkoxy, oxo or phenyl;

alkynyloxycarbonyl which is optionally substituted by fluorine, chlorine, hydroxyl, alkoxy, oxo or phenyl;

alkylthiocarbonyl which is optionally substituted by fluorine, chlorine, hydroxyl, alkoxy, oxo or phenyl;

alkenylthiocarbonyl which is optionally substituted by fluorine, chlorine, hydroxyl, alkoxy, oxo or phenyl;

alkylaminocarbonyl or dialkylaminocarbonyl which is optionally substituted by fluorine, chlorine, hydroxyl, alkoxy, oxo or phenyl;

alkenylaminocarbonyl or dialkenylaminocarbonyl which is optionally substituted by fluorine, chlorine, hydroxyl, alkoxy, oxo or phenyl;

alkylsulfonyl which ia optionally substituted by fluorine, chlorine, hydroxyl, alkoxy, alkylthio, oxo or phenyl;

alkenylsulfonyl which is optionally substituted by fluorine, chlorine, hydroxyl, alkoxy, oxo or phenyl;

or aryl, arylcarbonyl, aryl(thiocarbonyl), (arylthio)carbonyl, (arylthio)thiocarbonyl, aryloxycarbonyl, (arylamino)thiocarbonyl, arylsulfonyl, arylalkyl, arylalkenyl, arylalkynyl, arylalkylcarbonyl, arylalkenylcarbonyl or arylalkoxycarbonyl which is substituted by up to five radicals R$^7$ which are independent of each other, where R$^7$ is defined as above;

or heteroaryl, heteroarylalkyl, heteroarylalkenyl, heteroarylalkylcarbonyl or heteroarylalkenylcarbonyl which is substituted by up to three radicals R$^7$ which are independent of each other;

R$^5$ and R$^6$ are identical or different and are, independently of each other, hydrogen, carboxyl, alkyl which is optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl or alkoxycarbonyl;

alkenyl which is optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

alkynyl which is optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

cycloalkyl which is optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

cycloalkenyl which is optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

(cycloalkyl)-(alkyl) which is optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

(cycloalkenyl)-(alkyl) which is optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

alkylcarbonyl which is optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

alkenylcarbonyl which is optionally substituted by fluorine, chlorine or hydroxyl, alkoxy, oxo or phenyl;

(cycloalkyl)carbonyl which is optionally substituted by fluorine, chlorine or hydroxyl, alkoxy, oxo or phenyl;

(cycloalkenyl)carbonyl which is optionally substituted by fluorine, chlorine or hydroxyl, alkoxy, oxo or phenyl;

(cycloalkyl)-(alkyl)carbonyl which is optionally substituted by fluorine, chlorine or hydroxyl, alkoxy, oxo or phenyl;

(cycloalkenyl)-(alkyl)carbonyl which is optionally substituted by fluorine, chlorine or hydroxyl, alkoxy, oxo or phenyl;

alkyloxycarbonyl which is optionally substituted by fluorine, chlorine, bromine, hydroxyl, alkoxy, alkylamino, dialkylamino or alkylthio;

alkenyloxycarbonyl which is optionally substituted by fluorine, chlorine, hydroxyl, alkoxy, oxo or phenyl;

alkynyloxycarbonyl which is optionally substituted by fluorine, chlorine, hydroxyl, alkoxy, oxo or phenyl;

alkylthiocarbonyl which is optionally substituted by fluorine, chlorine, hydroxyl, alkoxy, oxo or phenyl;

alkenylthiocarbonyl which is optionally substituted by fluorine, chlorine, hydroxyl, alkoxy, oxo or phenyl;

alkylaminocarbonyl or dialkylaminocarbonyl which is optionally substituted by fluorine, chlorine, hydroxyl, alkoxy, oxo or phenyl;

alkenylaminocarbonyl or dialkenylaminocarbonyl which is optionally substituted by fluorine, chlorine, hydroxyl, alkoxy, oxo or phenyl;

alkylsulfonyl which is optionally substituted by fluorine, chlorine, hydroxyl, alkoxy, alkylthio, oxo or phenyl;

alkenylsulfonyl which is optionally substituted by fluorine, chlorine, hydroxyl, alkoxy, oxo or phenyl;

or aryl, arylcarbonyl, aryl(thiocarbonyl), (arylthio)carbonyl, (arylthio)thiocarbonyl, aryloxycarbonyl, (arylamino)thiocarbonyl, arylsulfonyl, arylalkyl, arylalkenyl, arylalkynyl, arylalkylcarbonyl, arylalkenylcarbonyl or arylalkoxycarbonyl which is substituted by up to five radicals $R^7$ which are independent of each other, where $R^7$ is defined as above;

or heteroaryl, heteroarylalkyl, heteroarylalkenyl, heteroarylalkylcarbonyl or heteroarylalkenylcarbonyl which is substituted by up to three radicals $R^7$ which are independent of each other, and $R^5$ and $R^6$ can also together be a carbocycle which is of a ring size of $C_3$–$C_8$ and which is linked to the quinoline system via the double bond.

$R^3$ and $R^4$ are identical or different and are, independently of each other, hydrogen, alkyl which is optionally substituted by fluorine, chlorine, hydroxyl, amino, mercapto, acyloxy, benzoyloxy, benzyloxy, phenoxy, alkoxy, alkylamino, dialkylamino, alkylthio, alkylsulfonyl, alkylsulfinyl, carboxyl or carbamoyl;

alkenyl which is optionally substituted by fluorine, chlorine, hydroxyl, amino, mercapto, acyloxy, benzoyloxy, benzyloxy, phenoxy, alkoxy, alkylamino, dialkylamino, alkylthio, alkylsulfonyl, alkylsulfinyl, carboxyl or carbamoyl;

cycloalkyl which is optionally substituted by fluorine, chlorine, hydroxyl, amino, mercapto, acyloxy, benzoyloxy, benzyloxy, phenoxy, alkoxy, alkylamino, dialkylamino, alkylthio, alkylsulfonyl, alkylsulfinyl, carboxyl or carbamoyl;

cycloalkenyl which is optionally substituted by fluorine, chlorine, hydroxyl, amino, mercapto, acyloxy, benzoyloxy, benzyloxy, phenoxy, alkoxy, alkylamino, dialkylamino, alkylthio, alkylsulfonyl, alkylsulfinyl, carboxyl or carbamoyl;

or aryl, arylalkyl, heteroaryl or heteroarylalkyl which is substituted by up to five radicals $R^7$ which are independent of each other, where $R^7$ is defined as above, $R^3$ and $R^4$ can also together be a carbocycle which is of a ring size of $C_3$–$C_8$ and which is linked to the quinoline system in a spiro manner;

$R^3$ and $R^4$ can also together be a radical $=C-Z^1Z^2$ which is linked via a double bond and where $Z^1$ and $Z^2$ have the meaning given above for $R^3$ and $R^4$, their optical isomers and diastereomers in pure form or in the form of their mixtures, and their addition salts and prodrugs, for application as pharmaceuticals.

The compounds mentioned above under 1)–5) are preferred for the application in accordance with the invention.

The present invention furthermore relates to the use of the compounds mentioned under 6) for preparing pharmaceuticals for treating viral diseases.

The alkyl groups mentioned in the preceding definitions may be straight-chain or branched. Unless otherwise defined, they preferably contain 1–8, particularly preferably 1–6, in particular 1–4, carbon atoms. Examples are the methyl, ethyl, propyl, 1-methylethyl, butyl, 1-methylpropyl, 2-methylpropyl and 1,1-dimethylethyl groups and the like.

The alkenyl groups mentioned in the preceding definitions may be straight-chain or branched and contain from 1 to 3 double bonds. Unless otherwise defined, these groups preferably contain 2–8, in particular 2–6, carbon atoms. Examples are the 2-propenyl, 1-methylethenyl, 2-butenyl, 3-butenyl, 2-methyl-2-propenyl, 3-methyl-2-butenyl, 2,3-dimethyl-2-butenyl, 3,3-dichloro-2-propenyl and pentadienyl groups and the like.

The alkynyl groups mentioned in the preceding definitions may be straight-chain or branched and contain from 1 to 3 triple bonds. Unless otherwise defined, they preferably contain 2–8, particularly preferably 3–6, carbon atoms. Examples are the 2-propynyl and 3-butynyl groups and the like.

The cycloalkyl and cycloalkenyl groups mentioned in the preceding definitions contain, unless otherwise defined, preferably 3–8, particularly preferably 4–6, carbon atoms. Examples are the cyclopropyl, cyclobutyl, cyclopentyl, cyclopentenyl, cyclohexyl or cyclohexenyl groups. The acyl groups mentioned in the preceding definitions may be aliphatic, cycloaliphatic or aromatic. Unless otherwise defined, they preferably contain 1–8, particularly 2–7, carbon atoms.

Exemplary acyl groups are the formyl, acetyl, chloroacetyl, trifluoroacetyl, hydroxyacetyl, glycyl, propionyl, butyryl, isobutyryl, pivaloyl, cyclohexanoyl or benzoyl groups.

Aromatic groups having 6–14 carbon atoms, in particular having 6–10 carbon atoms, for example phenyl and naphthyl, are preferred for the aryl groups mentioned in the preceding definitions.

O, S and N, for example, are particularly suitable heteroatoms in the abovementioned heterocyclic rings or heteroaryl groups, where, in the case of an N-containing ring which is saturated at this site, N—Z is present, in which Z is H or R2 having the respective, above-described definitions. Unless otherwise defined, the heterocyclic rings preferably have 1–15 carbon atoms and 1–6 heteroatoms, in particular 3–11 carbon atoms and 1–4 heteroatoms.

Thiophene, furan, pyridine, pyrimidine, indole, quinoline, isoquinoline, oxazole, isoxazole, thiazole or isothiazole, for example, are suitable for the heterocyclic rings or heteroaryl groups which were mentioned in the preceding definitions.

These definitions apply in the same manner to the heteroaryl in the heteroarylmethyl radical. Examples of the aralkyl groups cited in the preceding definitions are benzyl, phenylethyl, naphthylmethyl or styryl.

The abovementioned substituents $R^1$ to $R^7$ are preferably substituted 3-fold, particularly preferably 2-fold, in particular once, by the substituents cited in each case. The ranges for the individual substituents which were previously described as being preferred are likewise preferred for the respective composite substituent definitions (such as arylalkoxycarbonyl).

Depending on the different substituents, compounds of the formulae I and Ia can possess several asymmetric carbon atoms.

The invention therefore relates both to the pure stereoisomers and to mixtures thereof, such as, for example, the affiliated racemate.

The pure stereoisomers of the compounds of the formulae I and Ia can either be prepared directly, or can be separated subsequently, using known methods or in analogy with known methods.

The present invention furthermore relates to a process for preparing compounds of the formulae I) and Ia) as defined above under 1)–5), wherein A) in order to prepare compounds of the formulae I in which X is oxygen and Ia in which X is defined as under 1)–5)—with the exception of N—$R^2$ being N—H— and the radicals $R^1$, $R^2$, $R^3$, $R^4$, $R^5$ and $R^6$ are defined as under 1)–5), a compound of the formula II and Ia,

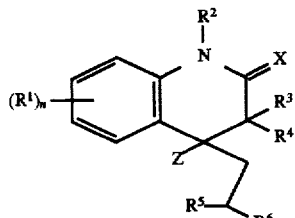

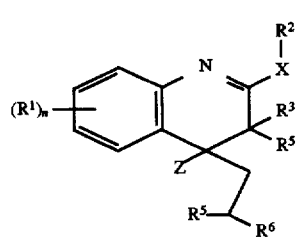

in which Z is a leaving group or an hydroxyl group, is heated in an inert solvent, where appropriate with an acidic or basic catalyst being added, B) in order to prepare compounds of the formulae II in which X is oxygen and Z is hydroxyl and IIa in which Z is hydroxyl, X is defined as under 1)–5)—with the exception of N—$R^2$ being N—H— and the radicals $R^1$, $R^2$, $R^3$, $R^4$, $R^5$ and $R^6$ are defined as under 1)–5), a compound of the formula III or IIIa,

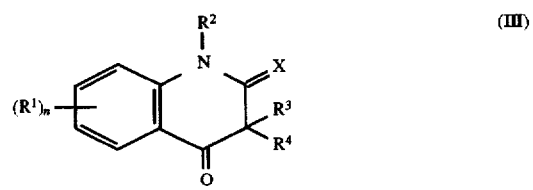

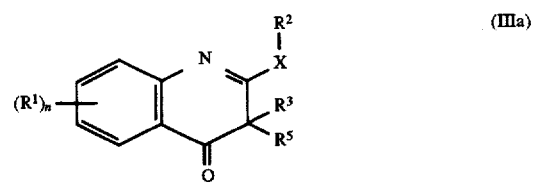

is reacted with a compound of the formula IV

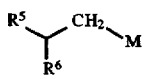

where M is a metal atom equivalent such as Li, —MgCl or —MgBr, or

C) in order to prepare compounds of the formulae I in which X is sulfur and $R^1$, $R^2$, $R^3$, $R^4$, $R^5$ and $R^6$ are defined as under 1)–5), by means of reacting a compound of the formula I, where X is oxygen and the definitions mentioned under 1)–5) apply to $R^1$, $R^2$, $R^3$, $R^4$, $R^5$ and $R^6$, with a sulfurization reagent, or wherein D) compounds of the formula I in which X is oxygen, $R^2$ is hydrogen and $R^1$, $R^3$, $R^4$, $R^5$ and $R^6$ are defined as under 1) to 5) are prepared by reacting with an alkylating reagent of the formula V

where $R^2$ has the meanings given under 1) to 5), with the exception of $R^2$ being hydrogen, and the leaving group K is, for example, a halogen atom such as chlorine or bromine or is a sulfonic ester group such as mesylate or triflate, or wherein E) a compound of the formula I in which $R^1$–$R^6$ are defined as under 1) to 5) and X is an oxygen atom or a sulfur atom is reacted with a compound of the formula $R^2$—$NH_2$ or $R^2$—O—$NH_2$ to form derivatives of the formula I in which $R^1$–$R^6$ are defined as under 1) to 5) and X is N—$R^2$ or N—O—$R^2$, or wherein F) a compound of the formula I in which $R^1$–$R^6$ are defined as under 1) to 5), with one of these radicals possessing an alkoxycarbonyl group, is reacted with a compound of the formula Met—OH, in which Met is an alkali metal atom or alkaline earth metal atom, to form derivatives of the formula I which possess a free carboxylic acid function, or wherein G) a compound of the formula I in which $R^1$=methoxy and $R^2$–$R^6$ are defined as under 1) to 5) and X is oxygen is reacted with trimethylsilyl iodide to form a compound of the formula I in which $R^1$=hydroxyl and the radicals $R^2$–$R^6$ and X are defined as above.

The abovementioned method A preferably proceeds under the following conditions:

halogen and sulfonic ester groups, such as mesylate or triflate, may be mentioned, by way of example, as leaving groups Z.

The reaction is expediently carried out in a solvent. Examples of suitable solvents are aromatic hydrocarbons such as toluene or xylene, water, lower alcohols such as methanol, ethanol, methyl glycol or 1-butanol, ethers such as tetrahydrofuran or glycol dimethyl ether, basic solvents such as pyridine or N-methylimidazole, or carboxylic acids such as acetic acid, or mixtures of these solvents.

It is advantageous for a suitable acidic or basic catalyst, for example p-toluenesulfonic acid, acetic acid, mineral acids, or salts such as sodium acetate, sodium carbonate or potassium carbonate, or pyridinium hydrochloride, to be present. The reaction temperature can be between 0° and 200° C., preferably at the boiling temperature of the solvent.

The abovementioned method B preferably proceeds under the following conditions:

The reactions are expediently carried out in a solvent. Examples of suitable solvents are acyclic dialkyl ethers such as diethyl ether or di-t-butyl ether, or cyclic ethers such as tetrahydrofuran. The reactions are expediently carried out at a temperature of from −78° C. up to the boiling temperature of the particular solvent, preferably between −30° C. and +25° C. In a reaction according to method B, a compound of the formula III or IIIa in which the substituents are defined as above is generally reacted with from at least 2 to 10, preferably from 2.2 to 4, molar equivalents of a compound of the formula IV, preferably a Grignard compound in which M is magnesium halide.

2,4-Bis(4-methoxyphenyl)-1,3-dithia-2,4-diphosphetane-2,4-disulfide (Lawessons reagent), bis(tricyclohexyltin)sulfide, bis(tri-n-butyltin)sulfide, bis(triphenyltin)sulfide, bis(trimethylsilyl)sulfide or phosphorus pentasulfide is preferably used as the sulfurization reagent for the reaction as previously described under C). The reaction is expediently carried out in an organic solvent or a mixture of solvents, at room temperature or higher, preferably at the boiling temperature of the reaction mixture, and as far as possible under anhydrous conditions. Examples which are suitable are carbon disulfide, toluene, xylene, pyridine or 1,2-dichloroethane. When the abovementioned tin or silyl sulfides are used, it is appropriate to carry out the sulfurization reaction in the presence of a Lewis acid such as boron trichloride.

When other carbonyl groups are present, these groups should, where appropriate, be protected prior to the sulfurization reaction with a suitable protective group using known methods, for example by means of acetalization.

In general, the abovementioned method D) is carried out in accordance with the following method:

The reaction is expediently carried out in a solvent. Examples of suitable solvents are aromatic hydrocarbons such as toluene or xylene, water, lower alcohols such as methanol, ethanol, methyl glycol or 1-butanol, ethers such as tetrahydrofuran or glycol dimethyl ether, and basic solvents such as pyridine or N-methylimidazole, or mixtures of these solvents.

In general, the abovementioned method E) is carried out in accordance with the following method:

The reaction is expediently carried out in a solvent. Examples of suitable solvents are aromatic hydrocarbons such as toluene or xylene, water, lower alcohols such as methanol, ethanol, methyl glycol or 1-butanol, ethers such as tetrahydrofuran or glycol dimethyl ether, and basic solvents such as pyridine or N-methylimidazole, or mixtures of these solvents.

In general, the abovementioned method F) is carried out in accordance with the following method:

The reaction is expediently carried out in a solvent. Examples of suitable solvents are mixtures of water and a lower alcohol such as methanol, ethanol, methyl glycol or 1-butanol. The reaction temperature can be between 0° and 200° C., preferably between 20° C. and the boiling temperature of the solvent mixture employed.

In general, the abovementioned method G) is carried out in accordance with the following method:

The reaction is expediently carried out in a solvent. Examples of suitable solvents are halogenated hydrocarbons such as chloroform, dichloromethane, carbon tetrachloride or 1,2-dichloroethane, or mixtures of these solvents. The reaction temperature can be between −20° and +200° C., preferably between +20° C. and the boiling temperature of the solvent employed.

The starting materials of the formulae III and IIIa are either known from the literature or can be prepared in accordance with methods which are described in the literature (e.g. Patent Application EP 93109965.9 and also A. B. Daruwala et al., J. Med. Chem. 1974, 17, 819, G. M. Coppola, Synthesis 1980, 505 and the literature cited in these publications). For example, synthesis of type III compounds in which X is oxygen can proceed from isatoic anhydrides of the formula VII, which are reacted with a compound of the formula VIII. In this context, M is a metal atom or a metal atom equivalent, preferably an alkaline earth metal or alkali metal, preferably lithium.

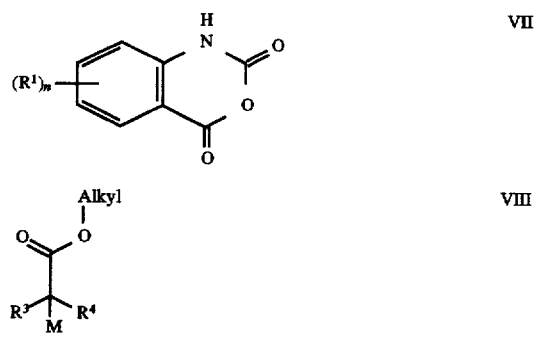

The novel pharmaceuticals may be employed enterally (orally) parenterally (intravenously), rectally, subcutaneously, intramuscularly or locally (topically). They may be administered in the form of solutions, powders (tablets, capsules including microcapsules), ointments (creams or gels) or suppositories. The liquid or solid fillers and extenders, solvents, emulsifiers, lubricants, taste corrigents, dyes and/or buffering substances which are pharmaceutically customary are suitable auxiliary substances for formulations of this nature.

As an expedient dosage, 0.1–10, preferably 0.2–8, mg/kg are administered once or several times daily per kg of body weight. The dosage units employed expediently depend on the particular pharmacokinetics of the substance or the pharmaceutical preparation which is used. The dosage unit of the novel compounds which is employed is, for example, 1–1500 mg, preferably 50–500 mg. The novel compounds may also be administered in combination with other antiviral agents, such as nucleoside analogs, protease inhibitors or adsorption inhibitors, and immunostimulants, interferons, interleukins and colony stimulating factors (e.g. GM-CSF, G-CSF, or M-CSF).

Activity tests
Testing preparations against HIV in cell culture
Description of the method
Medium
RPMI pH 6.8

The complete medium additionally contains 20% foetal calf serum and 40 IU/ml recombinant interleukin 2.

Cells

Lymphocytes which have been isolated from fresh donor blood by means of Ficoll® gradient centrifugation are cultured, at 37° C. for 36 h and under 5% $CO_2$, in complete medium in the added presence of 2 g/ml phytohemagglutinin (Wellcome). After the addition of 10% DMSO, the cells are frozen at a cell density of $5 \times 10^6$ and stored in liquid nitrogen. For the experiment, the cells are thawed, washed in RPMI medium and cultured for 3–4 days in complete medium.

Assay mixture

The preparations for testing were dissolved in DMSO at a concentration of 16.7 mg/ml and diluted to 1 mg/ml in complete medium. 0.4 ml of medium was initially introduced in 24-well multiwell plates. After 0.1 ml of the dissolved preparation had been added to the upper row of the plate, a geometrical dilution series was produced by transferring 0.1 ml on each occasion. Preparation-free controls always contained 0.4 ml of complete medium containing 0.5% DMSO.

Lymphocyte cultures having a cell count of $5 \times 10^5$ cells/ml were infected by adding a 1/50 volume of the supernatant from lymphocyte cultures infected with HIV. The titer of these culture supernatants was determined, by end point dilution, to be $1-5 \times 10^6$ infectious units/ml. After incubating at 37° C. for 30 min, the infected lymphocytes were centrifuged off and taken up once again in the same volume of medium. 0.6 ml of this cell suspension was added to each of the wells in the test plate. The assay mixtures were incubated at 37° C. for 3 days.

Assessment

The infected cell cultures were examined under the microscope for the presence of giant cells, which indicate that the virus is multiplying actively in the culture. The lowest preparation concentration at which no giant cells appeared was defined as the inhibitory concentration against HIV (MIC value). As a control, the presence of HIV antigen in the supernatants from the culture plates was determined using a test for HIV antigen in accordance with the manufacturer's (Organon) instructions.

Results

The results of this test are shown in Table 1.

TABLE 1

| Compound No. | MIC | IC-50 |
| --- | --- | --- |
| 1 | 1 µg/ml | >= 40 ng/ml |
| 2 | 0.1 µg/ml | ca. = 0.015 µg/ml |
| 3 | <0.08 µg/ml | 0.03 µg/ml |
| 4 | 0.0016 µg/ml | <0.32 ng/ml |
| 5 | 0.2 µg/ml | 0.04 µg/ml |
| 7 | <0.008 µg/ml | ca. 0.00032 µg/ml |
| 8 | 0.008 µg/ml | 0.0016 µg/ml |
| 10 | <0.04 mg/ml | 0.025 µg/mg |
| 13 | >0.2 µg/ml | 0.040 µg/ml |
| 14 | <0.008 µg/ml | 0.005 µg/ml |
| 16 | <0.2 µg/ml | ca. 0.03 µg/ml |
| 17 | <0.02 µg/ml | ca. 0.040 µg/ml |
| 18 | <0.008 µg/ml | 2 ng/ml |
| 19 | <0.04 mncg/ml | 0.008 µg/ml |
| 20 | <0.008 µg/ml | 0.0015 µg/ml |
| 28 | 0.008 µg/ml | ca. 0.01 µg/ml |
| 30 | <0.2 µg/ml | ca. 20 ng/ml |
| 32 | 0.2 µg/ml | ca. 80 ng/ml |
| 34 | <0.04 µg/ml | ca. 0.01 µg/ml |
| 36 | <0.2 µg/ml | ca. 10 ng/ml |
| 38 | <0.2 µg/ml | ca. 80 ng/ml |
| 41 | 0.2 µg/ml | ca. 0.2 µg/ml |
| 42 | <0.008 µg/ml | 0.002 µg/ml |
| 43 | 0.2 µg/ml | 0.05 µg/ml |

TABLE 1-continued

| Compound No. | MIC | IC-50 |
| --- | --- | --- |
| 44 | 0.2 µg/ml | 0.06 µg/ml |
| 45 | 0.004 µg/ml | 0.002 µg/ml |
| 47 | <0.08 µg/ml | ca. 0.015 µg/ml |
| 48 | <0.08 µg/ml | ca. 0.01 µg/ml |
| 49 | <0.02 µg/ml | ca. 0.002 µg/ml |
| 50 | <0.1 µg/ml | ca. 0.01 µg/ml |
| 51 | 0.02 µg/ml | ca. 0.002 µg/ml |
| 52 | 0.02 µg/ml | ca. 0.004 µg/ml |
| 53 | 0.02 µg/ml | ca. 0.002 µg/ml |
| 54 | 0.1 µg/ml | 0.05 µg/ml |
| 55 | <0.08 µg/ml | ca. 0.006 µg/ml |
| 58 | <0.1 µg/ml | ca. 0.02 µg/µl |
| 59 | <0.02 µg/ml | ca. 0.008 µg/ml |
| 60 | 0.0016 µg/ml | ca. 0.0003 µg/ml |
| 61 | 0.02 µg/ml | ca. 0.004 µg/ml |
| 66 | <0.1 µg/ml | ca. 0.01 µgµml |
| 67 | <0.1 µg/ml | ca. 0.02 µg/ml |
| 69 | <0.02 µg/ml | ca. 0.0018 µg/ml |
| 70 | 0.02 µg/ml | ca. 0.003 µg/ml |
| 71 | 0.0016 µg/ml | ca. 0.0005 ng/ml |
| 72 | <0.008 µg/ml | ca. 0.001 ng/ml |
| 73 | <0.04 µg/ml | 0.02 µg/ml |
| 74 | 0.04 µg/ml | 0.02 µg/µl |
| 75 | 0.004 µg/ml | ca. 0.0018 µg/ml |
| 77 | 0.2 µg/ml | ca. 0.03 µg/ml |
| 138 | >0.2 µg/ml | 0.030 µg/ml |
| 140 | 0.2 µg/ml | 0.006 µg/ml |
| 142 | <0.2 µg/ml | 0.004 µg/ml |
| 143 | >0.008 µg/ml | <0.008 µg/ml |

Investigation of the ability of the substances to inhibit the HIV reverse transcriptase The activity of the reverse transcriptase (RT) was measured by means of a scintillation proximity assay (SPA).

The reagent kit for the RT-SPA was obtained from Amersham/Buchler (Braunschweig). The RT enzyme (originating from HIV and cloned in *E. coli*) was provided by HT-Biotechnology LTD, Cambridge, UK.

Assay mixture

The test was carried out in accordance with the supplier's (Amersham) methods manual—with the following modifications:

bovine serum albumin was added to the assay buffer to a final concentration of 0.5 mg/ml.

The test was carried out in Eppendorf reaction tubes using a mixture volume of 100 ml.

The supplier's RT concentrate (5000 U/ml) was diluted in 20 mM tris-HCl buffer; pH 7.2; 30% glycerol to an activity of 15 U/ml.

The assay mixtures were incubated for 60 min (at 37° C.).

After the reaction had been stopped and "developed" using the bead suspension, 130 ml of assay mixture was transferred into 4.5 ml of 10 mM tris-HCl buffer; pH 7.4; 0.15M NaCl and the tritium activity was measured in a $\beta$ counter.

Testing the substances

In order to carry out a preliminary test for inhibitor activity, the substances were dissolved in DMSO (stock solution concentration=1 mg/ml) and tested at $10^{-1}$, $10^{-2}$, $10^{-3}$, etc. dilutions in DMSO.

In order to determine the $IC_{50}$ values, the stock solutions of inhibitor were further diluted in 50 mM tris-HCl buffer, pH 8, and tested at suitable concentrations.

The concentration giving rise to 50% inhibition of the enzyme was ascertained from the graphic depiction of RT activity versus log $C_{inh}$.

The results of the investigation are shown in Table 2.

TABLE 2

| Compound Number | Reverse Transcriptase Asaay IC-50 |
|---|---|
| 2 | 17 ng/ml (63 nM) |
| 3 | 27 ng/ml |
| 4 | 2 ng/ml (8 nM) |
| 5 | 115.5 ng/ml (479 nM) |
| 6 | 28.8 ng/ml (113 nM) |
| 7 | 5 ng/ml (18 nM) |
| 8 | 4 ng/ml (16 nM) |
| 10 | 31 ng/ml (116 nM) |
| 14 | 4 ng/ml (18 nM) |
| 18 | 15.2 nM (55 nM) |
| 19 | 10.3 ng/ml (37 nM) |
| 20 | 6.3 ng/ml (22 nM) |
| 24 | 66.3 ng/ml (270 nM) |
| 28 | 5.8 ng/ml (24 nM) |
| 42 | 2.6 ng/ml (9 nM) |
| 45 | 2.4 ng/ml (9 nM) |
| 48 | 14 ng/ml (54 nM) |
| 49 | 7 ng/ml (24 nM) |
| 51 | 6 ng/ml (23 nM) |
| 52 | 12 ng/ml (43 nM) |
| 53 | 13 ng/ml (44 nM) |
| 55 | 9 ng/ml (31 nM) |
| 59 | 14 ng/mg (46 nM) |
| 60 | 3 ng/ml (12 nM) |
| 61 | 17 ng/ml (62 nM) |
| 64 | 33 ng/ml (109 nM) |
| 66 | 19 ng/ml (70 nM) |
| 67 | 24 ng/ml (91 nM) |
| 68 | ca 10 ng/ml |
| 69 | 5 ng/ml (18 nM) |
| 70 | 6 ng/ml (21 nM) |
| 71 | 1 ng/ml (5 nM) |
| 73 | 8 ng/ml (30 nM) |
| 75 | <1 ng/ml |
| 138 | 61 ng/ml |
| 140 | 5 ng/ml |
| 142 | 38 ng/ml |

The present invention is explained in more detail by means of the following examples and by the content of the patent claims.

Preparation of the starting materials

EXAMPLE I

6-Chloro-3,3-dimethyl-1,3-dihydroquinolin-2,4-dione

A solution of 0.072 mol of lithium diisopropyl amide is prepared, at −70° C., from 7.3 g (0.072 mol) of diisopropyl amine in 100 ml of anhydrous tetrahydrofuran and 45 ml of a 1.6M solution of n-butyllithium in hexane. After warming briefly to −20° C., 3.48 g (0.03 mol) of ethyl isobutyrate are added at −70° C. The mixture is allowed to warm to 0C and is stirred for 30 min at this temperature. The lithium compound is then added dropwise to a suspension of 5.9 g (0.03 mol) of 5-chloroisatoic anhydride in 50 ml of anhydrous tetrahydrofuran which has been cooled down to −30° C. The reaction mixture is allowed to warm to 0° C. within the space of 1 hour, and the yellow reaction solution is then added to 400 ml of ice water. The mixture is extracted three times with ethyl acetate and the combined organic phases are washed once on each occasion with a saturated, aqueous solution of sodium hydrogen carbonate and a saturated, aqueous solution of sodium chloride; they are then dried over sodium sulfate and concentrated. After stirring with ether/pentane, 5.1 g (76%) of the desired compound, with an m.p. of 211°–212° C., are obtained after crystallizing from isopropanol.

$^1$H-NMR (200 MHz, $d_6$-DMSO):=1.30 (s, 6H), 7.11 (d, J=7.5 Hz, 1H), 7.6–7.7 (m, 2H), 10.87 ppm (s, 1H).

MS: (M+H)$^+$=224

EXAMPLE II

6-Chloro-3,3-diethyl-1,3-dihydroquinolin-2,4-dione

A suspension of 22.1 g (0.088 mol) of 4'-chloro-3,3-ethyl malonanilide in 220 g of polyphosphoric acid (approximately 84% $P_2O_5$) is heated to 80° C., while stirring vigorously, and stirred for 3 hours. During this time, the substance dissolves while coloring the solution yellow. After the reaction has finished, the reaction mixture is poured, while stirring, onto approximately 1000 ml of ice water, with the product separating out as a yellowish-white solid after a period of time. The solid is filtered off with suction, washed with water until neutral and dried under vacuum at 50° C.

Yield: 12.6 g (61%).

Melting point, 188° C. (after recrystallizing from isopropanol/heptane)

$^1$H-NMR (200 MHz, $d_6$-DMSO): δ=1.27 (s, 6H), 1.29 (t, J=7 Hz, 3H), 4.03 (q, J=7 Hz, 2H), 7.05 (d, J=8 Hz, 1H), 7.18 (m, 2H), 10.60 (br s, 1H)

MS: (M+H)$^+$=234

EXAMPLE III 3,3-Dimethyl-6-methoxy-1,3-dihydroquinolin-2,4-dione 16.2 g (80%) of the desired compound were obtained, in analogy with Example II, using 21.8 g (0.092 mol) of 4'-methoxy-3,3-dimethylmalonanilide. Melting point, 169°–170° C. (after recrystallizing from isopropanol).

$^1$H-NMR (200 MHz, $d_6$-DMSO):=1.31 (s, 6H), 3.78 (s, 3H), 7.02–7.28 (m, 3H), 10.62 ppm (s, 1H).

MS: (M+H)$^+$=220

Preparation of the end products

Example 1

4-n-Butyl-6-chloro-3,4-dihydro-3,3-dimethyl-4-hydroxyquinolin-2(1H)-one (P. 43)

4.47 g (20 mmol) of 6-chloro-3,3-dimethyl-1,3-dihydroquinolin-2,4-dione (Example I) are dissolved in 100 ml of absolute tetrahydrofuran and the solution is cooled down to −25° C. 30 ml (60 mmol) of a 2M solution of n-butylmagnesium bromide in THF are then added within the space of 30 minutes. After the addition is complete, the cooling is removed and the reaction mixture is stirred at 25° C. for 3 hours.

For the working up, the reaction solution is added to 200 ml of a saturated, aqueous solution of sodium chloride and the mixture is acidified (pH 3) with a 10 percent aqueous solution of citric acid. The mixture is then extracted by shaking three times with 100 ml of ethyl acetate and the combined organic phase is dried with sodium sulfate and concentrated under reduced pressure on a rotary evaporator. The pale yellow oil (7.2 g) which is obtained in this manner is purified by chromatography on silica gel with the mobile phase being n-heptane/ethyl acetate=2/1.

2.0 g (7.1 mmol) of 4-n-butyl-6-chloro-3,4-dihydro-3,3-dimethyl-4-hydroxyquinolin-2(1H)-one are obtained as a pale yellow oil (36% of theory). $R_F$ value=0.47 (silica gel plates: mobile phase=n-heptane/ethyl acetate=1:1)

¹H-NMR (200 MHz, d₆-DMSO):=0.73 (t, J=7.5 Hz), 0.86 (s, 3H), 1.13 (s, 3H), 0.98–1.35 (2 m, 6H), 1.36–1.79 (m, 2H), 5.11 (br s, 1H, OH group), 7.81 (d, J=8 Hz, 1H), 7.20 (dd, J=8 and 2.5 Hz, 1H), 7.35 (d, J=2.5 Hz, 1 Hz), 10.12 (br s, 1H)

MS: (M+H)⁺=282

Example 2

4-n-Butylene-6-chloro-3,4-dihydro-3,3-dimethylquinolin-2(1H)-one 1.4 g (4.97 mmol) of 4-n-butyl-6-chloro-3,4-dihydro-3,3-dimethyl-4-hydroxyquinolin-2(1H)-one (Example 1) are dissolved in 50 ml of absolute toluene and, after adding 100 mg of p-toluenesulfonic acid, the mixture is heated under reflux for 1 hour.

In order to work up the reaction mixture, 200 ml of ethyl acetate are added to it after the reaction is complete and the mixture has been cooled down to room temperature; the organic phase is then extracted with 100 ml of a saturated, aqueous solution of sodium bicarbonate and twice with 150 ml of water on each occasion. After the organic phase has been dried with sodium sulfate, it is concentrated under reduced pressure on a rotary evaporator. An oily, pale yellow residue is obtained which crystallizes when n-pentane is added.

Yield: 0.87 g (3.3 mmol; 66% of theory) of colorless crystals with a melting point of 144° C.; R_f=0.58, mobile phase: n-heptane/ethyl acetate=1/1

According to the ¹H-NMR spectrum, the reaction product is present as an E/Z diastereomeric mixture. According to HPLC (column: Nucleosil RP 18, 5 m, 200×4.6 mm; eluent: CH₃CN/buffer=40/60 using a buffer of water/methanol/H₃PO₄/NEt₃=750/403/0.5; flow rate: 1 ml/min), and also the ¹H-NMR spectrum, the EZ ratio is 75/25.

Separation of the E/Z diastereomers 600 mg of the diastereomeric mixture prepared above are chromatographed through Sephadex (Type LH-20, from Fluka) using methanol as the mobile phase:

In addition to mixed fractions, 320 mg of E-4-n-butylene-6-chloro-3,4-dihydro-3,3-dimethylquinolin-2(1H)-one, with a melting point of 157°–158° C., and 31 mg of Z-4-n-butylene-6-chloro-3,4-dihydro-3,3-dimethylquinolin-2(1H)-one, with a melting point of 170°–171° C., are obtained, with both fractions having purities which are in each case greater than 97%.

E-4-n-butylene-6-chloro-3,4-dihydro-3,3-dimethylquinolin-2(1H)-one (73)

¹H-NMR (200 MHz, d₆-DMSO):=0.87 (t, J=7.5 Hz, 3H), 1.18 (s, 6H), 1.44 (qt, J=7.5 Hz, 2H), 2.25 (q, J=7.5 Hz, 2H), 5.73 (t, J=7.5 Hz, 1H), 6.93 (d, J=10 Hz, 1H), 7.28 (s, 1H), 7.33 (d, J=10 Hz, 1H), 10.28 (br s, 1H)

MS: (M+H)⁺=264

Z-4-n-butylene-6-chloro-3,4-dihydro-3,3-dimethylquinolin-2(1H)-one (74)

¹H-NMR (200 MHz, d₆-DMSO):=0.93 (t, J=7.5 Hz, 3H), 1.36 (s, 6H), 1.48 (qt, J=7.5 Hz, 2H), 2.41 (q, J=7.5 Hz, 2H), 5.88 (t, J=7.5 Hz, 1 H), 6.86 (d, J=10 Hz, 1H), 7.23 (dd, J=2.5 and 10 Hz, 1H), 7.42 (d, J=2.5 Hz, 1H), 10.32 (br s, 1H)

MS: (M+H)⁺=264

Example 3

E-4-n-butylene-6-chloro-3,4-dihydro-3,3-dimethylquinolin-2(1H)-thione (75)

200 mg (0.76 mmol) of E-4-n-butylene-6-chloro-3,4-dihydro-3,3-dimethylquinolin-2(1H)-one (Example 2) are dissolved in 20 ml of absolute toluene, and 170 mg (0.42 mmol) of Lawesson's reagent (2,4-bis(4-methoxyphenyl)-1,3-dithia-2,4-diphosphetane-2,4-disulfide) are added to this solution; the reaction mixture is then heated at 100° C. for 2 hours.

After the reaction is complete, the solvent is stripped off in vacuo and the residue is chromatographed on silica gel. When n-heptane/ethyl acetate, mixed in a ratio of 2:1, is used as the eluent, 140 mg (66%) of the desired product are isolated (yellowish crystals with a melting point of 160° C.).

¹H-NMR (200 MHz, d₆-DMSO):=0.87 (t, J=7 Hz, 3H), 1.27 (s, 6H), 1.44 (qt, J=7 Hz, 2H) 2.26 (q, J=7 Hz, 2H), 5.86 (t, J=7 Hz, 1H), 7.18 (d, J=9.5 Hz, 1H), 7.33–7.40 (2 m, 2H), 12.33 (br s, 1H)

MS: (M+H)⁺=280

Example 4

4-n-Butyl-3,4-dihydro-3,3-dimethyl-4-hydroxy-6-methoxyquinolin-2(1H)-one (Compound 23)

2 g (9 mmol) of 3,3-dimethyl-6-methoxy-1,3-dihydroquinolin-2,4-dione (Example III) are dissolved in absolute tetrahydrofuran, and 13 ml of a 2 molar solution of n-butylmagnesium chloride in THF are added to this solution at a temperature of −20° C. The mixture is subsequently allowed to come to room temperature and is then stirred for 2 hours.

The reaction solution is then added to 250 ml of a saturated, aqueous solution of sodium chloride and the mixture is acidified (pH 3) with a 20% aqueous solution of citric acid. This mixture is extracted by shaking three times with 100 ml of ethyl acetate and the combined organic phases are dried with sodium sulfate; they are then concentrated under reduced pressure on a rotary evaporator. The pale yellow oil which is obtained in this manner is purified by chromatography on silica gel (mobile phase, n-heptane/ethyl acetate=2/1).

1.2 g (48% of theory) of a colorless oil are obtained.

¹H-NMR (200 MHz, d₆-DMSO): 0.71 (t, J=7.5 Hz, 3H), 0.85 (s, 3H), 0.97–1.69 (3 m, 6H), 1.10 (s, 3 H), 3.71 (s, 3H), 4.92 (br s, 1 OH), 6.72 (2 ps s, 2H), 6.95 (ps s, 1H), 9.78 (br s, 1H)

MS: (M+H)⁺=278

Example 5

E/Z-4-n-butylene-3,4-dihydro-3,3-dimethyl-6-methoxyquinolin-2(1H)-one (41)

600 mg (2 mmol) of 4-n-butyl-3,4-dihydro-3,3-dimethyl-4-hydroxy-6-methoxyquinolin-2(1H)-one (Example 4) are dissolved in 40 ml of absolute toluene, and a spatula tip of p-toluenesulfonic acid is added; the mixture is then heated at 100° C. for 3 hours. After the reaction mixture has been cooled down to room temperature, the organic phase is dried over sodium sulfate and the solvent is removed under reduced pressure on a rotary evaporator. The reaction product crystallizes out when the solvent is removed.

Yield: 0.39 g (73% of theory), melting point 121°–122° C.

MS: (M+H)⁺=260

According to ¹H-NMR (200 MHz, d₆-DMSO), the reaction product is composed of an E/Z diastereomeric mixture. The E/Z ratio of the diastereomers is approximately 10:1. The data for the main component are found to be:=0.89 (t, J=7.5, 3H), 1.16 (s, 3H), 1.45 (tq, J=7.5 Hz, 2H), 2.29 (dt, J=7.5 Hz, 2H), 3.73 (s, 3H), 5.64 (t, J=7.5 Hz, 1H), 6.84 (br s, 3H), 9.97 (br s, 1H).

Example 6

E/Z-4-n-butylene-3,4-dihydro-3,3-dimethyl-6-methoxyquinolin-2(1H)-thione (42) and E-4-n-butylene-3,4-dihydro-3,3-dimethyl-6-methoxyquinolin-2 (1H)-thione (79)

0.23 g (0.89 mmol) of E/Z-4-n-butylene-3,4-dihydro-3,3-dimethyl-6-methoxyquinolin-2(1H)-one (see Example 5) are dissolved in 12 ml of absolute toluene, and 0.22 g of Lawesson's reagent(2,4-bis-(4-methoxyphenyl)-1,3-dithia-2,4-diphosphetane-2,4-disulfide) is added. The reaction mixture is heated at 100° C. for 3 hours.

After the reaction is complete, the solvent is distilled in vacuo and the residue is chromatographed on silica gel. When n-heptane/ethyl acetate, mixed in a ratio of 3:1, is used as the eluent, 239 mg (94%) of the target compound are isolated (colorless crystals with a melting point of 133°–134° C.).

MS: (M+H)⁺=276

According to the ¹H-NMR spectrum and examination by HPLC, a 70:30 E/Z diastereomeric mixture is present.

In order to isolate the E diastereomer, 120 mg of the E/Z diastereomeric mixture is chromatographed through Sephadex (Type LH-20) using methanol as the mobile phase. 70 mg of E-4-n-butylene-3,4-dihydro-3,3-dimethyl-6-methoxyquinolin-2(1H)-thione are isolated with a purity of 97% (HPLC analysis) (melting point: 135°–136° C.).

E-4-n-butylene-3,4-dihydro-3,3-dimethyl-6-methoxyquinolin-2(1H)-thione (79)

$^1$H-NMR (200 MHz, $d_6$-DMSO): 0.88 (t, J=7 Hz, 3H), 1.26 (s, 3H), 1.43 (tq, J=7 Hz, 2H), 2.27 (dt, J=7 Hz, 2H), 3.76 (s, 3H), 5.81 (t, J=7 Hz, 1H), 6.85 (m, 1H), 6.88 (dd, J=2 and 8.5 Hz, 1H), 7.08 (d, J=8.5 Hz, 1H), 12.14 (br s, 1H)

MS: (M+H)⁺=276

Example 7

4-n-Butyl-3,3-cylopentylidene-3,4-dihydro-4-hydroxyquinolin-2(1H)-one (P. 5)

4.3 g (0.02 mol) of 3,3-cyclopentylidenequinolin-2,4(1H,3H)-dione (prepared in accordance with example 1 but using ethyl cyclopentanecarboxylate instead of ethyl isobutyrate) are dissolved in 100 ml of absolute tetrahydrofuran, and 30 ml of n-butylmagnesium chloride (2M solution in THF) are added at a temperature of −30° C. After the addition is complete, the mixture is subsequently stirred at 25° C. for 3 hours. The reaction solution is then added to 200 ml of a saturated, aqueous solution of sodium chloride and the mixture is acidified (pH 3) with a 10% aqueous solution of citric acid. This mixture is extracted three times with 150 ml of ethyl acetate and the combined organic phases are dried with sodium sulfate; they are then concentrated under reduced pressure on a rotary evaporator. The pale yellow oil which is obtained in this manner is purified by chromatography on silica gel using a mobile phase of n-heptane/ethyl=2/1. 2.62 g (48%) of the desired reaction product are obtained (melting point, 95°–97° C.).

$^1$H-NMR (200 MHz, $d_6$-DMSO):=0.7 (t, J=7.5 Hz, 3H), 0.96–2.20 (m, 14H), 4.93 (br s, 1H), 6.79 (dd, J=7 and 1 Hz, 1H), 6.95 (dt, J=twice 7 and once 1 Hz, 1H), 7.14 (dt, J=twice 7 and once 1 Hz, 1H), 7.37 (dd, J=7 and 1 Hz, 1H), 9.85 (br s, 1H)

MS: (M+H)⁺=274

Example 8

E/Z-4-n-butylene-3,3-cyclopentylidene-3,4-dihydroquinolin-2(1H)-one (6)

2 g (7.3 mmol) of 4-n-butyl-3,3-cyclopentylidene-3,4-dihydro-4-hydroxyquinolin-2(1H)-one (see Experiment 7) are dissolved in 100 ml of absolute toluene, and this solution is heated under reflux for 2 hours together with a spatula tip of p-toluenesulfonic acid. After the reaction is complete, the solvent is concentrated under reduced pressure on a rotary evaporator and the residue is recrystallized from n-pentane.

Yield: 1.75 g (94%); Melting point 115°–117° C.

MS: (M+H)⁺=256

Example 9

E/Z-4-n-butylene-3,3-cyclopentylidene-3,4-dihydroquinolin-2(1H)-thione (8) and E-4-n-butylene-3,3-cyclopentylidene-3,4-dihydroquinolin-2(1H)-thione (80)

1 g (3.9 mmol) of E/Z-4-n-butylene-3,3-cyclopentylidene-3,4-dihydroquinolin-2(1H)-one (see Example 8) are dissolved in 100 mol of abs. toluene, and 0.89 g of Lawesson's reagent (2,4-bis-(4-methoxyphenyl)-1,3-dithia-2,4-diphosphetane-2,4-disulfide) is added to the solution. The reaction mixture is heated under ref lux for three hours.

After the reaction is complete, the solvent is stripped off in vacuo and the residue is chromatographed on silica gel. The desired reaction product can be isolated by using n-heptane/ethyl acetate, mixed in the ratio of 3:1, as the eluent and then crystallizing from n-pentane.

Yield: 0.51 g (48%); melting point: 81°–83° C. According to the ¹H-NMR spectrum and also investigation by HPLC, an 82:18 E/Z diastereomeric mixture is present.

In order to isolate the E diastereomer, 300 mg of the E/Z diastereomeric mixture are chromatographed through Sephadex (type LH-20) using methanol as the mobile phase. In addition to mixed fractions of the two diastereomers, 150 mg of E-4-n-butylene-3,3-cyclopentylidene-3,4-dihydroquinolin-2(1H)-thione are obtained with a melting point of 80°–81° C.

$^1$H-NMR (200 MHz, $d_6$-DMSO):=0.86 (t, J=7 Hz, 3H), 1.43 (tq, J=7 Hz, 2H), 1.45–1.85 (3 m, 6H), 2.06–2.18 (m, 2H), 2.23 (td, J=7 Hz, 2H), 5.74 (t, J=7 Hz, 1H), 7.08–7.19 (m, 2H), 7.25–7.36 (m, 2H), 12.18 (br s, 1H)

MS: (M+H)⁺=272

Example 10

3,4-Dihydro-3,3-dimethyl-4-hydroxyl-4-(3-methyl-3-propen-1-yl)quinolin-2(1H)-one (compound 38)

A corresponding solution of 2-methyl-2-propenylmagnesium chloride in THF is prepared from 1.1 g (45 mmol) of magnesium filings and 2.34 ml (23.8 mmol) of 3-chloro-2-methyl-1-propene as well as 30 ml of absolute THF as the solvent. 2.2 g (11.9 mmol) of 3,3-dimethyl-6-methoxy-1,3-dihyroquinolin-2,4-dione (compound from Example III), which were previously dissolved in 25 ml of abs. THF, are added to this solution at 25° C.

For the working up, the reaction solution is subsequently added to 100 ml of a saturated, aqueous solution of sodium chloride, and the mixture is acidified (pH 3) with a 20% aqueous solution of citric acid. This mixture is then extracted three times with 100 ml of ethyl acetate on each occasion and the combined organic phase is dried with sodium sulfate and concentrated under reduced pressure on a rotary evaporator. The pale yellow crude product which is obtained in this manner is purified by chromatography on silica gel; mobile phase, n-heptane/ethyl acetate=2/1.

1.27 g of the desired compound are obtained as a pale yellow oil (yield 44%).

MS: (M+H)⁺=278

Example 11

3,4-Dihydro-3,3-dimethyl-4-(3-methyl-3-propenylene) quinolin-2(1H)-one (82)

1 g (4 mmol) of 3,4-dihydro-3,3-dimethyl-4-hydroxy-4-(3-methyl-3-propen-1-yl)quinolin-2(1H)-one (Example 10) is dissolved in 60 ml of absolute toluene, and 20 mg of p-toluenesulfonic acid are added. The reaction mixture is heated at 100° C. for three hours and the course of the reaction is monitored by thin layer chromatography.

After the reaction mixture has been cooled down to room temperature, it is extracted with 100 ml of a saturated solution of sodium bicarbonate and then three times with 100 ml of water on each occasion. After the organic phase has been dried over magnesium sulfate and concentrated under reduced pressure on a rotary evaporator, the remaining oily residue is stirred up with n-pentane.

After some time, the reaction product, 3,4-dihydro-3,3-dimethyl-4-hydroxy-4-(3-methyl-3-propen-1-yl)quinolin-2(1H)-one, crystallizes out in the form of colorless crystals.

Yield: 0.81 g (89% theory); melting point: 151°–153° C.

$^1$H-NMR (200 MHz, d$_6$-DMSO):=1.19 (2 s, 6H), 1.73 (2, 3H), 4.85 (br s, 1H), 4.98 (br s, 1H), 6.19 (br s, 1H), 6.89 (d, J=7.5 Hz, 1H), 6.93 (ddd, J=7.5 (twice) and 1 Hz), 7.21 (ddd, J=1 and 7.5 Hz (twice), 7.34 (d, J=7.5 Hz, 1H), 10.96 (br s, 1H)

MS: M+H)⁺=228

Example 12

3,4-Dihydro-3,3-dimethyl-4-(3-methyl-3-propenylene)quinolin-2(1H)-thione (83)

0.6 g (2.6 mmol) of 3,4-dihydro-3,3-dimethyl-4-(3-methyl-3-propenylene)quinolin-2(1H)-one (see Example 11) is dissolved in 20 ml of abs. toluene, and 0.64 g of Lawesson's reagent (2,4-bis(4-methoxyphenyl)-1,3-dithia-2,4-diphosphetane-2,4-disulfide) is added to this solution. The reaction mixture is heated under reflux for 8 hours.

For the working up, the solvent is removed under reduced pressure on a rotary evaporator and the crude product is purified by chromatography on silica gel (mobile phase: n-heptane/ethyl acetate=3/1). The reaction product then crystallizes out when the solvent is removed under reduced pressure on a rotary evaporator.

Yield: 320 mg (51% theory); melting point, 140°–142° C.

$^1$H-NMR (200 MHz, D$_6$-DMSO):=1.31 (2 s, 6H), 1.72 (s, 3H), 4.83 (br s, 1H), 4.98 (br s, 1H), 6.33 (br s, 1H), 7.08 (ddd, J=14.8 and 1 Hz, 1H), 7.26 (m, 1H), 7.38 (d, J=8 Hz, 1H), 12.25 (br s, 1H)

MS: (M+H)⁺=244

Example 13

E/Z-4-n-Butylene-6-chloro-3,4-dihydro-1,3,3-trimethylquinolin-2(1H)-one (91)

264 mg of 4-n-butylene-6-chloro-3,4-dihydro-3,3-dimethylquinolin-2(1H)-one (see Example 2) are dissolved in 20 ml of absolute N,N-dimethylformamide, and 53 mg of sodium hydride (50% suspension in oil) are added to this solution at a temperature of 25° C. and while stirring. After the hydrogen evolution is complete, 280 mg of methyl iodide are added to the reaction mixture, which is then stirred at 25° C. for one hour. A colorless precipitate separates out. For the working up, the solvent is distilled off on a rotary evaporator under an oil pump vacuum and the remaining residue is extracted with water/ethyl acetate. The combined organic phase is subsequently dried over Na$_2$SO$_4$ and the extraction agent is removed under reduced pressure on a rotary evaporator. A pale yellow, oily residue is obtained which is purified by chromatography on silica gel using n-heptane/ethyl acetate=3/1 as the mobile phase.

Yield: 270 mg (97% theory), pale yellow oil $^1$H-NMR (200 MHz, d$_6$-DMSO):=0.86 (t, J=7.5 Hz, 3H), 1.14 (s, 6H), 1.44 (tq, J=7.5 Hz, 2H), 2.25 (dt, J=7.5 Hz, 2H), 3.25 (s, 3H), 5.68 (t, J=7.5 Hz, 1H), 7.18 (d, J=9 Hz, 1H), 7.28–7.44 (m, 2H)

MS: (M+H)⁺=278

Example 14

E/Z-4-n-Butylene-6-chloro-3,4-dihydro-1,3,3-trimethylquinolin-2(1H)-thione (87)

150 mg of E/Z-4-n-butylene-6-chloro-3,4-dihydro-1,3,3-trimethylquinolin-2(1H)-one (see Example 13) are reacted with Lawesson's reagent in accordance with Example 12. The resulting crude product is purified chromatographically by means of column chromatography on silica gel using n-heptane/ethyl acetate=7/1 as the mobile phase.

Yield: 110 mg, pale yellow oil $^1$H-NMR (200 MHz, d$_6$-DMSO):=0.88 (t, J=7.5 Hz, 3H), 1.25 (s, 6H), 2.45 (tq, J=7.5 Hz, 2H), 2.23 (dt, J=7.5 Hz, 2H), 3.80 (s, 3H), 5.83 (t, J=7.5 Hz, 1H), 7.27–7.55 (m, 3H)

MS: (M+H)⁺=294

Example 15

E/Z-4-n-Butylene-6-chloro-3,4-dihydro-1,3,3-trimethylquinolin-2(1H)-on-2-oxime (90)

1.5 g (5.4 mmol) of E/Z-4-n-butylene-6-chloro-3,4-dihydro-3,3-trimethylquinolin-2(1H)-one (see Example 2) are dissolved in 40 ml of absolute ethanol, and 751 mg (10.8 mmol) of hydroxylamine hydrochloride and 1.5 ml (10.8 mmol) of triethylamine are added to this solution while stirring. The reaction mixture is stirred at 25° C. for 48 hours.

For the working up, the reaction mixture is concentrated under reduced pressure on a rotary evaporator and the remaining residue is extracted with ethyl acetate/water. The combined organic phase is dried with Na$_2$SO$_4$ and the extraction agent is removed under reduced pressure on a rotary evaporator. The remaining residue crystallizes out when n-pentane is added.

Yield: 1.43 g (95% theory), colorless crystals with a melting point of 163°–165° C.

$^1$H-NMR (200 MHz, d$_6$-DMSO):=0.89 (t, J=7.5 Hz, 3H), 1.19 (s, 6H), 1.43 (tq, J=7.5 Hz, 2H), 2.25 (dt, J=7.5 Hz, 2H), 5.51 (t, J=7.5 Hz, 1H), 7.05–7.21 (m, 3H), 9.03 (s, 1H), 9.74 (s, 1H)

MS: (M+H)⁺=279

Example 16

E/Z-4-Butylene-3,4-dihydro-3,3-dimethyl-6-hydroxyquinolin-2(1H)-one (106)

1.5 g (5.8 mmol) of E/Z-4-butylene-3,4-dihydro-3,3-dimethyl-6-methoxyquinolin-2(1H)-one (Example 5) are dissolved in 80 ml of 1,2-dichloroethane, and 5 ml of trimethylsilyl iodide are added to this solution at 25° C. The mixture is subsequently heated under reflux for 12 hours.

For the working up, 100 ml of methanol are added to the reaction mixture while cooling with ice, and the solvent is removed under reduced pressure on a rotary evaporator. The remaining residue is purified by chromatography on silica gel (eluent: ethyl acetate/n-heptane which are mixed in a ratio of 1 to 3). A Sephadex column (type LH-20, from Fluka) with methanol as the mobile phase may suitably be used for purifying the reaction product still further.

Yield: 220 mg (16%); melting point 162°–163° C.

$^1$H-NMR (200 MHz, $d_6$-DMSO): δ=0.89 (t, 3H), 1.13 (s, 6H), 1.44 (tq, 2H), 2.26 (dt, 2H), 5.60 (t, 1H), 6.8–6.58 (3m, 3H), 9.14 (br, s, 10H), 10.83 (s, 1NH)

MS: $(M+H)^+$=246

Example 17

4-E-n-Butylen-1-oxycarbonylmethyl-3,4-dihydro-6,7-dimethoxy-3,3-dimethylquinolin-2(1H)-one (123)

0.35 g (0.97 mmol) of 4-E-n-butylene-3,4-dihydro-6,7-dimethoxy-3,3-dimethyl-1-methoxycarbonylmethylquinolin-2(1H)-one (compound 122, for preparation compare Tables 3 and 4) is dissolved in 20 ml of ethanol, and 0.8 g of NaOH pellets, which were dissolved beforehand in 20 ml of water, are added to this solution. The reaction mixture is heated under reflux for 3 hours.

For the working up, the reaction mixture is concentrated under reduced pressure on a rotary evaporator down to 1/3 of its original volume and the residue is acidified with 2N aqueous hydrochloric acid. After extracting with ethyl acetate, the organic phase is dried over sodium sulfate and the solvent is distilled off on a rotary evaporator. After adding 10 ml of n-pentane, the reaction product crystallizes out in the form of colorless crystals.

Yield: 0.28 mg (83% theory), melting point 143°–144° C.

$^1$H-NMR (200 MHz, $d_6$-DMSO): δ=0.89 (t, 3H), 1.16 (s, 6H), 1.46 (qt, 2H), 2.31 (dt, 2H), 3.75 (s, 3H), 3.81 (s, 3H), 4.56 (s, 2H), 5.6 (t, 1H), 6.61 (s, 1H), 6.88 (s, 1H), 12.76 (br, s, 1H)

MS: $(M+H)^+$=348

Example 18

4-Cyclopentyl-3,3-dimethyl-3,4-dihydro-4-hydroxyquinolin-2(1H)-one

A solution of 0.18 mol of cyclopentyllithium in n-pentane is prepared from lithium powder and cyclopentyl chloride. This solution is added, at a temperature of –70° C., to a solution of 4.73 g (25 mmol) of 3,3-dimethyl-1,3-dihydroquinolin-2,4-dione, synthesized in accordance with Example I but using isatoic anhydride and ethyl isobutyrate as the starting components, dissolved in 200 ml of abs. tetrahydrofuran, and, after having been stirred for one hour at this temperature, the reaction mixture is then warmed to 0° C.

For the working up, 100 ml of a 20% aqueous solution of citric acid are added and the reaction mixture is then added to water and this mixture is extracted with ethyl acetate. After having been dried with sodium sulfate, the extraction agent is distilled off under reduced pressure on a rotary evaporator. The pale yellow oil which results as the crude product is purified by means of chromatography on silica gel (mobile phase: n-heptane/ethyl acetate=2/1). The reaction product is subsequently recrystallized from n-pentane.

Yield: 4.95 mg (76% theory), colorless crystals with a melting point of 188°–189° C.

$^1$H-NMR (200 MHz, $d_6$-DMSO): δ=0.60–0.78 (m, 1H), 0.93 (s, 3H), 1.02–1.50 (m, 5H), 1.17 (s, 3H), 1.66–1.81 (m, 1H), 2.21–2.05 (m, 1H), 4.84 (s, 10H), 6.78 (d, 1H), 6.97 (t, 1H), 7.16 (dt, 1H), 7.40 (dt, 1H), 9.91 (s, 1NH)

MS: $(M+H)^+$=260

(With regard to liberating the OH group using trimethylsilyl iodide, see, for example, M. B. Jung and M. A. Lyster, J. Org. Chem. 42, 3764 (1977)).

Table 3 below gives an overview of the synthesized compounds. All the derivatives were characterized by means of their $^1$H-NMR spectra, their mass spectra and their melting points. Many of the compounds are E/Z diastereomeric mixtures, which, in some cases, were resolved by Sephadex chromatography (type LH-20, mobile phase methanol; see Example 2). In the table, diastereomeric mixtures are indicated by the bond concerned being drawn with a wavy line. In general, these mixtures contain an excess of the E compound.

TABLE 3

Synthesized derivatives of the formulae (I) and (Ia)

| Compound number | Structure | Melting point (in °C.) | Preparation in accordance with Ex. Yield in % | Prepared from |
|---|---|---|---|---|
| 1 | (structure: chloro-substituted benzene fused with N-H ring bearing S, CH₃, CH₃, =CH₂ substituents) | 167 | cf. Examples 2 and 3. Total yield for both steps 8% | P. 1 |

TABLE 3-continued

Synthesized derivatives of the formulae (I) and (Ia)

| Compound number | Structure | Melting point (in °C.) | Preparation in accordance with Ex. Yield in % | Prepared from |
|---|---|---|---|---|
| 2 | | 144 | see Example 2, 66% | P. 43 |
| 3 | | 164 | cf. Example 2, 77% | P. 3 |
| 4 | | oil | cf. Example 3, 97% | 3 |
| 5 | | 89–100 | cf. Example 8, 32% | P. 4 |
| 6 | | 115–117 | see Example 8, 94% | P. 5 |
| 7 | | 116–120 | cf. Example 9, 75% | 5 |

TABLE 3-continued

Synthesized derivatives of the formulae (I) and (Ia)

| Compound number | Structure | Melting point (in °C.) | Preparation in accordance with Ex. Yield in % | Prepared from |
|---|---|---|---|---|
| 8 | 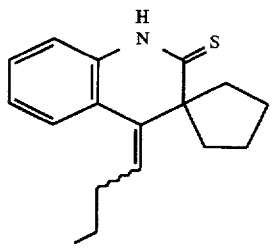 | 81–83 | see Example 9, 48% | 6 |
| 9 | 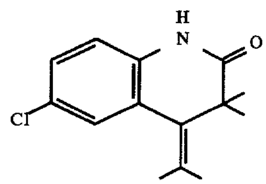 | 176 | cf. Example 2, 21% | P. 7 |
| 10 | 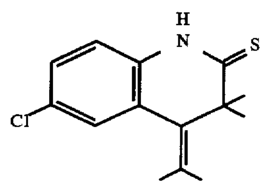 | 156 | cf. Example 3, 59% | 9 |
| 11 | 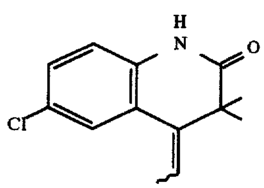 | 168 | cf. Example 2, 91% | P. 8 |
| 12 | 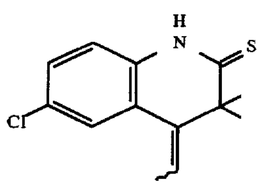 | oil | cf. Example 3, 94% | 11 |
| 13 | 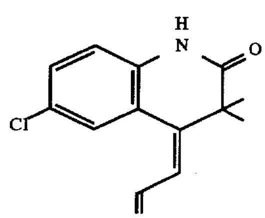 | 251–253 | cf. Example 2, 46% | P. 2 |
| 14 | 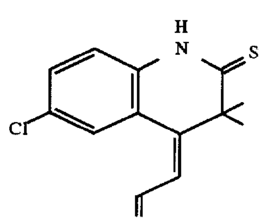 | 172 | cf. Example 3, 31% | 13 |

TABLE 3-continued

Synthesized derivatives of the formulae (I) and (Ia)

| Compound number | Structure | Melting point (in °C.) | Preparation in accordance with Ex. Yield in % | Prepared from |
|---|---|---|---|---|
| 15 | | 120 | cf. Example 2, 74% | P. 13 |
| 16 | | 119 | cf. Example 3, 57% | 15 |
| 17 | | 165 | cf. Example 2, 78% | P. 14 |
| 18 | | 169 | cf. Example 3, 56% | 17 |
| 19 | | 160 | cf. Example 2, 68% | P. 15 |
| 20 | | 162 | cf. Example 3, 90% | 19 |

TABLE 3-continued

Synthesized derivatives of the formulae (I) and (Ia)

| Compound number | Structure | Melting point (in °C.) | Preparation in accordance with Ex. Yield in % | Prepared from |
|---|---|---|---|---|
| 21 | 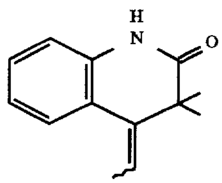 | 156 | cf. Example 2, 76% | P. 9 |
| 22 | 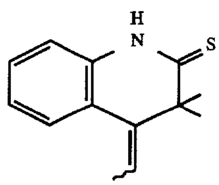 | 135 | cf. Example 3, 97% | 21 |
| 23 | 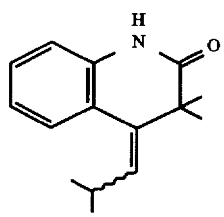 | 178–179 | cf. Example 2, 32% | P. 16 |
| 24 | 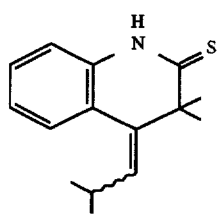 | 163–164 | cf. Example 3, 94% | 23 |
| 25 | 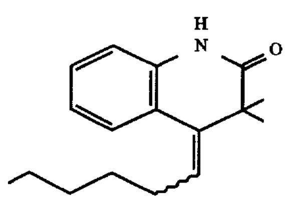 | 94–96 | cf. Example 2, 83% | P. 17 |
| 26 | 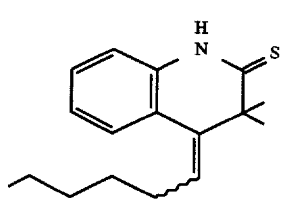 | 108–109 | cf. Example 3, 94% | 25 |
| 27 | 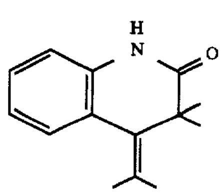 | 196 | cf. Example 2, 18% | P. 18 |

TABLE 3-continued

Synthesized derivatives of the formulae (I) and (Ia)

| Compound number | Structure | Melting point (in °C.) | Preparation in accordance with Ex. Yield in % | Prepared from |
|---|---|---|---|---|
| 28 | 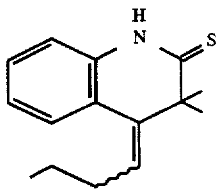 | 94–96 | cf. Example 3, 88% | 85 |
| 29 | 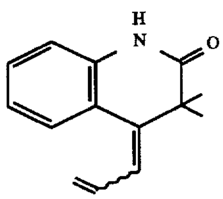 | 199–201 | cf. Example 2, 62% | P. 10 |
| 30 | 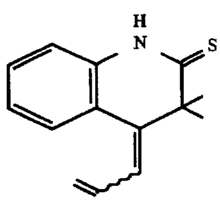 | 158–159 | cf. Example 3, 73% | 29 |
| 31 | 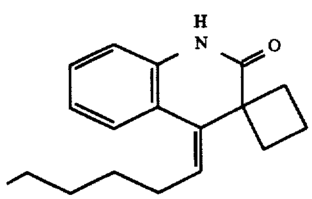 | 87–88 | cf. Example 8, 35% | P. 12 |
| 32 | 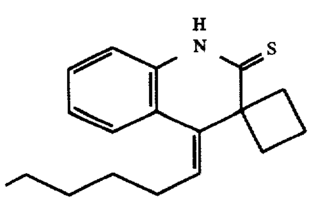 | 85–87 | cf. Example 9, 46% | 31 |
| 33 | 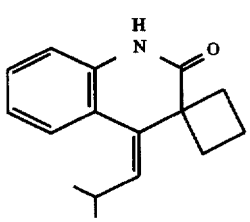 | 158–160 | cf. Example 8, 26% | P. 6 |
| 34 | 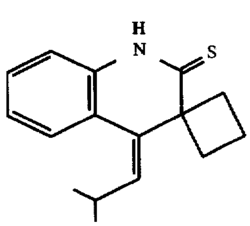 | 190–191 | cf. Example 9, 94% | 33 |

TABLE 3-continued

Synthesized derivatives of the formulae (I) and (Ia)

| Compound number | Structure | Melting point (in °C.) | Preparation in accordance with Ex. Yield in % | Prepared from |
|---|---|---|---|---|
| 35 | | 132–133 | cf. Example 2, 56% | P. 21 |
| 36 | | 100 | cf. Example 3, 70% | 35 |
| 37 | | 139–141 | cf. Example 2, 88% | P. 11 |
| 38 | | 132–133 | cf. Example 3, 61% | 37 |
| 39 | | 296 | cf. Example 2, 75% | P. 22 |
| 40 | | 167–168 | cf. Example 3, 63% | 39 |
| 41 | | 121–122 | see Example 5, 73% | P. 23 |

TABLE 3-continued

Synthesized derivatives of the formulae (I) and (Ia)

| Compound number | Structure | Melting point (in °C.) | Preparation in accordance with Ex. Yield in % | Prepared from |
|---|---|---|---|---|
| 42 | | 133–134 | see Example 6, 94% | 41 |
| 43 | | 152–154 | cf. Example 2, 61% | P. 24 |
| 44 | | 130–132 | cf. Example 2, 86% | P. 25 |
| 45 | | 128–130 | cf. Example 3, 100% | 40 |
| 46 | | 156 | cf. Example 2, 86% | P. 26 |
| 47 | | 159 | cf. Example 3, 87% | 46 |
| 48 | | 83 | cf. Example 2, 56% | P. 27 |

TABLE 3-continued

Synthesized derivatives of the formulae (I) and (Ia)

| Compound number | Structure | Melting point (in °C.) | Preparation in accordance with Ex. Yield in % | Prepared from |
|---|---|---|---|---|
| 49 | | 119 | cf. Example 3, 79% | 48 |
| 50 | | 126 | cf. Example 2, 35% | P. 28 |
| 51 | | 138 | cf. Example 3, 61% | 50 |
| 52 | | 82 | cf. Example 2, 54% | P. 29 |
| 53 | | 119 | cf. Example 3, 98% | 52 |
| 54 | | 137 | cf. Example 2, 95% | P. 30 |

TABLE 3-continued

Synthesized derivatives of the formulae (I) and (Ia)

| Compound number | Structure | Melting point (in °C.) | Preparation in accordance with Ex. Yield in % | Prepared from |
| --- | --- | --- | --- | --- |
| 55 | | 140 | cf. Example 3, 88% | 54 |
| 56 | | 155–158 | cf. Example 2, 75% | P. 31 |
| 57 | | 161–164 | cf. Example 3, 81% | 56 |
| 58 | | 155 | cf. Example 2, 94% | P. 32 |
| 59 | | 142–144 | cf. Example 3, 92% | 58 |
| 60 | | 163–165 | cf. Example 15, 95% | 75: an E/Z diastereomeric mixture was employed |

TABLE 3-continued

Synthesized derivatives of the formulae (I) and (Ia)

| Compound number | Structure | Melting point (in °C.) | Preparation in accordance with Ex. Yield in % | Prepared from |
|---|---|---|---|---|
| 61 | | 165–167 | cf. Example 3, 96% | 43 |
| 62 | | 117–118 | cf. Example 2, 81% | P. 20 |
| 63 | | 113–115 | cf. Example 8, 42% | P. 33 |
| 64 | | 115–116 | cf. Example 3, 82% | 62 |
| 65 | | 166–168 | cf. Example 2, 64% | P. 44 |
| 66 | | 140–141 | cf. Example 2, 81% | P. 34 |

TABLE 3-continued

Synthesized derivatives of the formulae (I) and (Ia)

| Compound number | Structure | Melting point (in °C.) | Preparation in accordance with Ex. Yield in % | Prepared from |
|---|---|---|---|---|
| 67 | | 127–129 | cf. Example 8, 96% | P. 35 |
| 68 | | 144–147 | cf. Example 3, 54% | 65 |
| 69 | | 166–167 | cf. Example 3, 88% | 66 |
| 70 | | 118–120 | cf. Example 9, 72% | P. 67 |
| 71 | | 185 | cf. Example 3 | 4 (diastereomers separated using Sephadex/MeOH) |
| 72 | | 145 | cf. Example 3 | 4 (diastereomers separated using Sephadex/MeOH) |

TABLE 3-continued

Synthesized derivatives of the formulae (I) and (Ia)

| Compound number | Structure | Melting point (in °C.) | Preparation in accordance with Ex. Yield in % | Prepared from |
|---|---|---|---|---|
| 73 | | 157–158 | see Example 2 | P. 43 |
| 74 | | 170–171 | see Example 2 | P. 43 |
| 75 | | 160 | see Example 3 | 73 |
| 76 | | 129–130 | cf. Example 3, 25% | 27 |
| 77 | | 164–166 | cf. Example 8, 41% | P. 36 |
| 78 | | 137–139 | cf. Example 8, 79% | P. 63 |
| 79 | | 135–136 | see Example 6 | 42 (diastereomers separated using Sephadex/ MeOH) |

TABLE 3-continued

Synthesized derivatives of the formulae (I) and (Ia)

| Compound number | Structure | Melting point (in °C.) | Preparation in accordance with Ex. Yield in % | Prepared from |
|---|---|---|---|---|
| 80 | | 80–81 | see Example 9 | 8 (diastereomers separated using Sephadex/MeOH) |
| 81 | | 116–117 | cf. Example 9 | 7 (diastereomers separated using Sephadex/MeOH) |
| 82 | | 151–153 | see Example 11, 89% | P. 38 |
| 83 | | 140–142 | see Example 12, 51% | 82 |
| 84 | | 148 | see Example 16, 21% | 41 |
| 85 | | 132–133 | cf. Example 2, 92% | P. 19 |

TABLE 3-continued

Synthesized derivatives of the formulae (I) and (Ia)

| Compound number | Structure | Melting point (in °C.) | Preparation in accordance with Ex. Yield in % | Prepared from |
| --- | --- | --- | --- | --- |
| 86 | 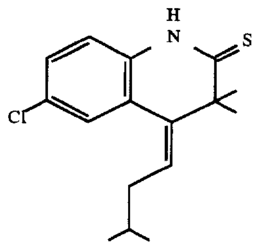 | 177 | cf. Example 3 | 20 (diastereomers separated using Sephadex/MeOH) |
| 87 | 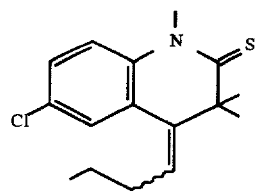 | oil | see Example 14, 97% | 91 |
| 88 | 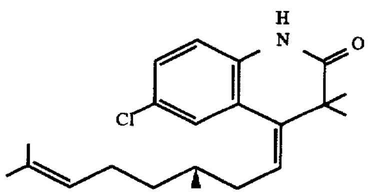 | oil | cf. Example 2, 84% | P. 39 |
| 89 | 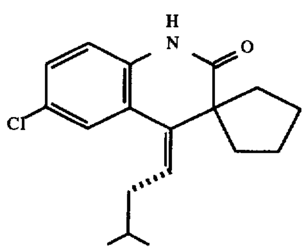 | 154–156 | cf. Example 8, 48% | P. 37 |
| 90 | 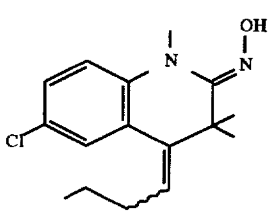 | 163–165 | see Example 15, 95% | 87 |
| 91 | 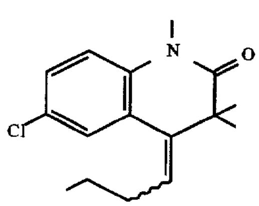 | oil | see Example 13, 97% | 2 |

TABLE 3-continued

Synthesized derivatives of the formulae (I) and (Ia)

| Compound number | Structure | Melting point (in °C.) | Preparation in accordance with Ex. Yield in % | Prepared from |
|---|---|---|---|---|
| 92 | 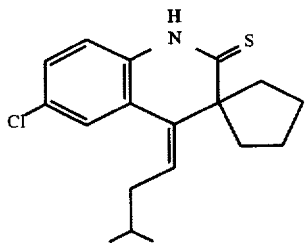 | 144–145 | cf. Example 9, 98% | 89 |
| 93 | 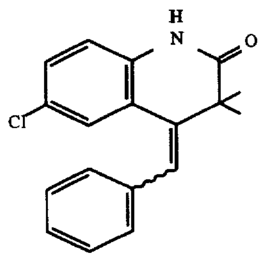 | 196–198 | cf. Example 2, 76% | P. 41 |
| 94 | 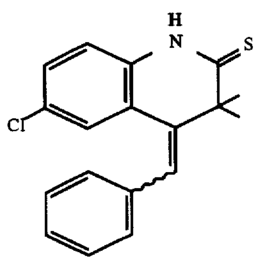 | 161–163 | cf. Example 3, 95% | 93 |
| 95 | 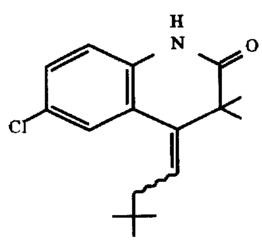 | 155 | cf. Example 2, 55% | P. 42 |
| 96 | 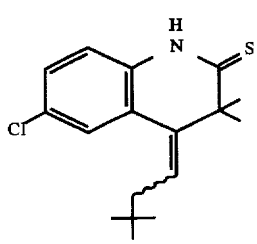 | 152 | cf. Example 3, 88% | 95 |
| 97 | 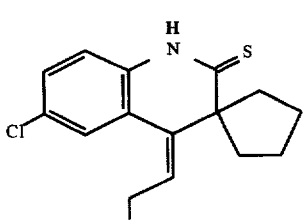 | 154 | cf. Example 6, 70% (diastereomers separated using sephadex/methanol) | 77 |

TABLE 3-continued

Synthesized derivatives of the formulae (I) and (Ia)

| Compound number | Structure | Melting point (in °C.) | Preparation in accordance with Ex. Yield in % | Prepared from |
|---|---|---|---|---|
| 98 | | oil | cf. Example 13, 83% (using allyl bromide in place of methyl iodide) | 2 |
| 99 | | oil | cf. Example 13, 75% | 75 |
| 100 | | oil | cf. Example 13, 95% (using benzyl bromide in place of methyl iodide) | 2 |
| 101 | | oil | cf. Example 13, 57% (using acetyl chloride in place of methyl iodide) | 2 |
| 102 | | 151–153 | cf. Example 2, 77% | P. 45 |
| 103 | | 124–126 | cf. Example 6, 79% (diastereomers separated using Sephadex/ methanol) | 102 |

TABLE 3-continued

Synthesized derivatives of the formulae (I) and (Ia)

| Compound number | Structure | Melting point (in °C.) | Preparation in accordance with Ex. Yield in % | Prepared from |
|---|---|---|---|---|
| 104 | | 138–139 | cf. Example 15, 60% | 103 |
| 105 | | 77–79 | cf. Example 2, 92% | P. 46 |
| 106 | | 162–163 | see Example 16 | 41 |
| 107 | | 129–133 | cf. Example 6, 40% | 106 |
| 108 | | oil | cf. Example 2, 35% | P. 44 |
| 109 | | oil | cf. Example 6, 38% | 100 |
| 110 | | 195–199 | cf. Example 5, 66% | P. 47 |

TABLE 3-continued

Synthesized derivatives of the formulae (I) and (Ia)

| Compound number | Structure | Melting point (in °C.) | Preparation in accordance with Ex. Yield in % | Prepared from |
|---|---|---|---|---|
| 111 | 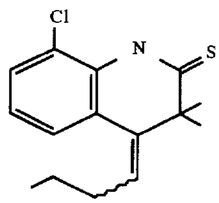 | oil | cf. Example 6, 85% | 105 |
| 112 | 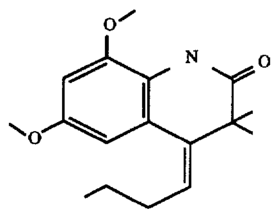 | 140–141 | cf. Example 5, 78% | P. 48 |
| 113 | 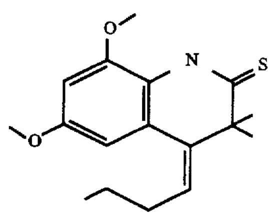 | 121–122 | cf. Example 6, 87% | 112 |
| 114 | 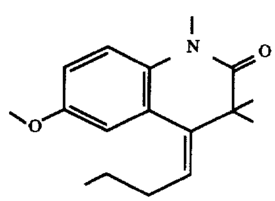 | oil | cf. Example 13, 41% (diastereomers separated using Sephadex/methanol) | 41 |
| 115 | 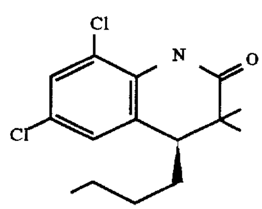 | 130–134 | cf. Example 5, 44% | P. 50 |
| 116 | 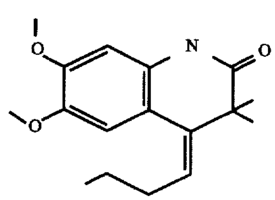 | 133–134 | cf. Example 5, 94% | P. 49 |
| 117 | 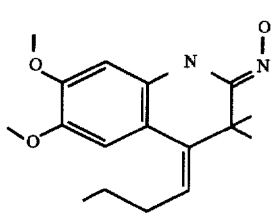 | 157–158 | cf. Example 15, 85% | 120 |

TABLE 3-continued

Synthesized derivatives of the formulae (I) and (Ia)

| Compound number | Structure | Melting point (in °C.) | Preparation in accordance with Ex. Yield in % | Prepared from |
|---|---|---|---|---|
| 118 | | oil | see Example 13, 84% (using K₂CO₃ as a base; solvent, acetone) | 41 |
| 119 | | 81–83 | cf. Example 13, 59% (using acetyl chloride in place of methyl iodide) | 116 |
| 120 | | 110–112 | cf. Example 6, 89% | 116 |
| 121 | | 105–107 | cf. Ex. 13, 70% (using bromoacetonitrile in place of methyl iodide) | 116 |
| 122 | | oil | cf. Ex. 13, 68% (using ethyl bromoacetate in place of methyl iodide) | 116 |
| 123 | | 143–144 | see Example 17 | 122 |

TABLE 3-continued

Synthesized derivatives of the formulae (I) and (Ia)

| Compound number | Structure | Melting point (in °C.) | Preparation in accordance with Ex. Yield in % | Prepared from |
|---|---|---|---|---|
| 124 | | oil | cf. Ex. 13, 40% (using benzoyl chloride in place of methyl iodide) | 3 |
| 125 | | 216–218 | cf. Ex. 5, 96% | P. 51 |
| 126 | | 146–148 | cf. Ex. 5, 32% | P. 52 |
| 127 | | 178–179 | cf. Ex. 5, 92% | P. 53 |
| 128 | | 196–197 | cf. Ex. 6, 91% | 127 |
| 129 | | 162 | cf. Ex. 5, 25% | P. 54 |

TABLE 3-continued

Synthesized derivatives of the formulae (I) and (Ia)

| Compound number | Structure | Melting point (in °C.) | Preparation in accordance with Ex. Yield in % | Prepared from |
|---|---|---|---|---|
| 130 | | 171 | cf. Ex. 6, 93% | 129 |
| 131 | | 127 | cf. Ex. 5, 21% | P. 55 |
| 132 | | 150 | cf. Ex. 6, 82% | 131 |
| 133 | | 216 | cf. Ex. 5, 96% | P. 56 |
| 134 | | 222 | cf. Ex. 6, 75% | 133 |
| 135 | | 181 | cf. Ex. 5, 83% | P. 57 |

TABLE 3-continued

Synthesized derivatives of the formulae (I) and (Ia)

| Compound number | Structure | Melting point (in °C.) | Preparation in accordance with Ex. Yield in % | Prepared from |
|---|---|---|---|---|
| 136 | | 214 | cf. Ex. 6, 55% | 135 |
| 137 | | 185–186 | cf. Ex. 5, 54% | P. 58 |
| 138 | | 181–182 | cf. Ex. 5, 49% | P. 59 |
| 139 | | 144–146 | cf. Ex. 5, 35% | P. 60 |
| 140 | | 192–193 | cf. Ex. 6, 80% | 138 |
| 141 | | 178–179 | cf. Ex. 6, 49% | 139 |

TABLE 3-continued

Synthesized derivatives of the formulae (I) and (Ia)

| Compound number | Structure | Melting point (in °C.) | Preparation in accordance with Ex. Yield in % | Prepared from |
|---|---|---|---|---|
| 142 | *(structure: 4-chlorophenyl quinoline-thione with ethyl ester side chain)* | 158–159 | cf. Ex. 6, 78% | 126 |
| 143 | *(structure: 4-fluorophenyl quinoline-thione with cyclopentylidene)* | 205–207 | cf. Example 6, 94% | 137 |

In general, the derivatives listed in Table 3 are prepared from the relevant compounds of the formula II or IIa in which Z is hydroxyl. Table 4 provides an overview of all the precursors which have thus far been synthesized. The corresponding substituted quinolinediones which are used as starting compounds for preparing the hydroxy compounds may be prepared by the methods in Examples I–III.

TABLE 4

Synthesized precursors

| Structure | M.p. | Ex. No. | Preparation method |
|---|---|---|---|
| *(4-chlorophenyl amide with OH)* | | 142 | P. 1 | In analogy with experiment 1 |
| *(4-chlorophenyl amide with OH and allyl)* | | 143 | P. 2 | In analogy with experiment 1 |
| *(4-chlorophenyl amide with OH and ethyl)* | | 166 | P. 3 | In analogy with experiment 1 |

TABLE 4-continued

Synthesized precursors

| Structure | M.p. | Ex. No. | Preparation method |
|---|---|---|---|
| 2-(1-hydroxy-1-(1-hydroxycyclobutyl)pentyl)anilide | 130–131 | P. 4 | In analogy with experiment 1 |
| 2-(1-hydroxy-1-(1-hydroxycyclopentyl)pentyl)anilide | 95–97 | P. 5 | see experiment 7; 48% |
| 2-(1-hydroxy-1-(1-hydroxycyclobutyl)-3-methylbutyl)anilide | 139–140 | P. 6 | In analogy with experiment 1 |
| 4-chloro-2-(1-hydroxy-2,2,3-trimethylbutyl)anilide | 195 | P. 7 | In analogy with experiment 1 |
| 4-chloro-2-(1-ethyl-1-hydroxy-2,2-dimethylbutyl)anilide | 195 | P. 8 | In analogy with experiment 1 |
| 2-(1-ethyl-1-hydroxy-2,2-dimethylbutyl)anilide | 161–162 | P. 9 | In analogy with experiment 1 |
| 2-(1-hydroxy-2,2-dimethyl-1-vinylpropyl)anilide | oil | P. 10 | In analogy with experiment 1 |

TABLE 4-continued

Synthesized precursors

| Structure | M.p. | Ex. No. | Preparation method |
|---|---|---|---|
| (structure) | 122–124 | P. 11 | In analogy with experiment 1 |
| (structure) | oil | P. 12 | In analogy with experiment 1 |
| (structure) | oil | P. 13 | In analogy with experiment 1 |
| (structure) | oil | P. 14 | In analogy with experiment 1 |
| (structure) | oil | P. 15 | In analogy with experiment 1 |
| (structure) | oil | P. 16 | In analogy with experiment 1 |
| (structure) | oil | P. 17 | In analogy with experiment 1 |

TABLE 4-continued

Synthesized precursors

| Structure | M.p. | Ex. No. | Preparation method |
|---|---|---|---|
| [structure: 2-aminophenyl with C(CH₃)₂-C(OH)(iPr) group, amide] | oil | P. 18 | In analogy with experiment 1 |
| [structure: 2-aminophenyl with C(CH₃)₂-C(OH)(butyl) group, amide] | 120 | P. 19 | In analogy with experiment 1 |
| [structure: 4-methoxy-2-aminophenyl with C(CH₃)₂-C(OH)(hexyl) group, amide] | oil | P. 20 | In analogy with experiment 1 |
| [structure: 4-trifluoromethoxy-2-aminophenyl with C(CH₃)₂-C(OH)(butyl) group, amide] | oil | P. 21 | In analogy with experiment 1 |
| [structure: 2-aminophenyl with cyclopentyl-C(OH)(iPr) group, amide] | 86–87 | P. 22 | In analogy with experiment 1 |
| [structure: 4-methoxy-2-aminophenyl with C(CH₃)₂-C(OH)(butyl) group, amide] | oil | P. 23 | see Example 4, 48% |
| [structure: 4-methoxy-2-aminophenyl with C(CH₃)₂-C(OH)(isobutyl) group, amide] | oil | P. 24 | In analogy with experiment 1 |

TABLE 4-continued

Synthesized precursors

| Structure | M.p. | Ex. No. | Preparation method |
|---|---|---|---|
| [3,4-dihydroquinolin-2(1H)-one with 5-methoxy, 3-methyl, 4-OH, 4-propyl substituents] | oil | P. 25 | In analogy with experiment 1 |
| [3,4-dihydroquinolin-2(1H)-one with 5-ethoxy, 3-methyl, 4-OH, 4-isobutyl substituents] | 163 | P. 26 | In analogy with experiment 1 |
| [3,4-dihydroquinolin-2(1H)-one with 3-ethyl, 4-OH, 4-butyl substituents] | 124 | P. 27 | In analogy with experiment 1 |
| [3,4-dihydroquinolin-2(1H)-one with 3-ethyl, 4-OH, 4-propyl substituents] | 106 | P. 28 | In analogy with experiment 1 |
| [3,4-dihydroquinolin-2(1H)-one with 3-ethyl, 4-OH, 4-isopentyl substituents] | 120 | P. 29 | In analogy with experiment 1 |
| [3,4-dihydroquinolin-2(1H)-one with 6-ethoxy, 3,3-dimethyl, 4-OH, 4-butyl substituents] | 132 | P. 30 | In analogy with experiment 1 |
| [3,4-dihydroquinolin-2(1H)-one with 6-ethoxy, 3-methyl, 4-OH, 4-ethyl substituents] | 137 | P. 31 | In analogy with experiment 1 |

TABLE 4-continued

| Synthesized precursors | | | |
|---|---|---|---|
| Structure | M.p. | Ex. No. | Preparation method |
| [structure: 6-ethoxy-4-methyl-4-(3-methylbutyl)-4-hydroxy-3,4-dihydroquinolin-2(1H)-one] | 129 | P. 32 | In analogy with experiment 1 |
| [structure: spirocyclobutane quinolinone with butyl and OH] | 171–173 | P. 33 | In analogy with experiment 1 |
| [structure: 6-methoxy-4-methyl-4-(3-methylbutyl)-4-hydroxy-3,4-dihydroquinolin-2(1H)-one] | oil | P. 34 | In analogy with experiment 1 |
| [structure: spirocyclopentane quinolinone with 3-methylbutyl and OH] | 121–123 | P. 35 | In analogy with experiment 1 |
| [structure: 6-chloro spirocyclopentane quinolinone with propyl and OH] | 85–86 | P. 36 | In analogy with experiment 1 |
| [structure: 6-chloro spirocyclopentane quinolinone with 3-methylbutyl and OH] | oil | P. 37 | In analogy with experiment 1 |

TABLE 4-continued

Synthesized precursors

| Structure | M.p. | Ex. No. | Preparation method |
|---|---|---|---|
| [structure] | oil | P. 38 | see experiment 10 |
| [structure] | oil | P. 39 | In analogy with experiment 1 |
| [structure] | oil | P. 40 | In analogy with experiment i |
| [structure] | 189–190 | P. 41 | In analogy with experiment 1 |
| [structure] | oil | P. 42 | In analogy with experiment 1 |
| [structure] | oil | p. 43 | Example 1 |

TABLE 4-continued
Synthesized precursors
| Structure | M.p. | Ex. No. | Preparation method |
|---|---|---|---|
| 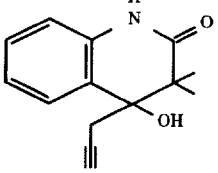 | oil | P. 44 | In analogy with experiment 1 |
| 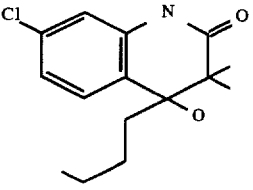 | oil | P. 45 | In analogy with experiment 1 |
| 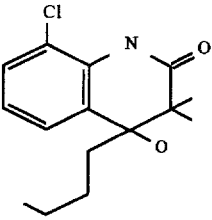 | 177–178 | P. 46 | In analogy with experiment 1 |
| 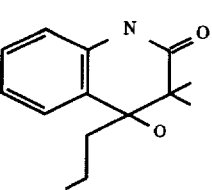 | 63 | P. 47 | In analogy with experiment 1 |
| 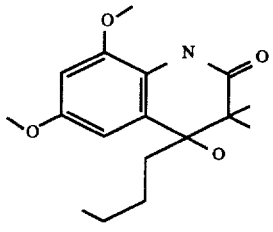 | 119–120 | P. 48 | In analogy with experiment 1 |
| 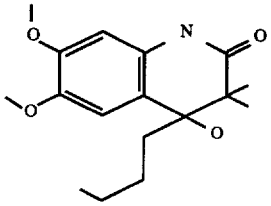 | 138–139 | P. 49 | In analogy with experiment 1 |
| 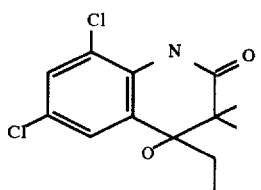 | oil | P. 50 | In analogy with experiment 1 |

TABLE 4-continued

Synthesized precursors

| Structure | M.p. | Ex. No. | Preparation method |
|---|---|---|---|
| (structure) | 224–226 | P. 51 | In analogy with experiment 1 |
| (structure) | 177 | P. 52 | In analogy with experiment 18 |
| (structure) | 188–189 | P. 53 | Experiment 18 |
| (structure) | oil | P. 54 | In analogy with experiment 18 |
| (structure) | 111 | P. 55 | In analogy with experiment 18 |
| (structure) | 165 | P. 56 | In analogy with experiment 18 |
| (structure) | 183 | P. 57 | In analogy with experiment 18 |

TABLE 4-continued

Synthesized precursors

| Structure | M.p. | Ex. No. | Preparation method |
|---|---|---|---|
| 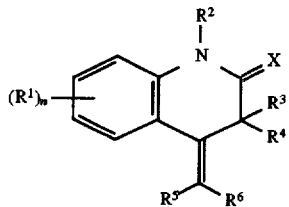 | oil | P. 58 | In analogy with experiment 18 |
| 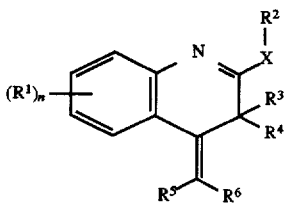 | 141 | P. 59 | In analogy with experiment 18 |
| | oil | P. 60 | In analogy with experiment 18 |

We claim:

1. A compound of the formula I, (I)

or one of its tautomeric forms of the formula, (Ia)

in which:

n is zero, one, two, three or four, the individual substituents $R^1$ are, independently of each other, fluorine, chlorine, bromine, iodine, trifluoromethyl, trifluoromethoxy, hydroxyl, alkyl, cycloalkyl, alkoxy, alkoxy(alkoxy), alkylthio, alkylsulfinyl, alkylsulfonyl, acyl, acyloxy, carbamoyl, carboxyl, alkyloxycarbonyl, hydroxysulfonyl or sulfamoyl, or a phenyl, phenoxy, phenoxycarbonyl, phenylthio, phenylsulfinyl, phenylsulfonyl, phenoxysulfonyl, phenylsulfonyloxy, anilinosulfonyl, phenylsulfonyl-amino, or benzoyl radical which is substituted by up to five radicals $R^7$ which are independent of each other, where $R^7$ is fluorine, chlorine, bromine, iodine, cyano, trifluoromethyl, trifluoromethoxy, nitro, amino, azido, alkyl, cycloalkyl, alkoxy, alkylthio, alkylsulfinyl, alkylsulfonyl, alkylamino, dialkylamino, or alkyloxycarbonyl, X is oxygen, sulfur, or N—OH, $R^2$ is hydrogen or alkyl which is unsubstituted or substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl or alkoxycarbonyl;

alkenyl which is unsubstituted or substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

alkynyl which is unsubstituted or substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

cycloalkyl which is unsubstituted or substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

cycloalkenyl which is unsubstituted or substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

(cycloalkyl)-(alkyl) which is unsubstituted or substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

(cycloalkenyl)-(alkyl) which is unsubstituted or substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

$R^5$ and $R^6$ are identical or different and are, independently of each other, hydrogen, carboxyl, alkyl which is unsubstituted or substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl or alkoxycarbonyl;

alkenyl which is unsubstituted or substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

alkynyl which is unsubstituted or substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

cycloalkyl which is unsubstituted or substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

cycloalkenyl which is unsubstituted or substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

(cycloalkyl)-(alkyl) which is unsubstituted or substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

(cycloalkenyl)-(alkyl) which is unsubstituted or substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

alkyloxycarbonyl which is unsubstituted or substituted by fluorine, chlorine, bromine, hydroxyl, alkoxy, alkylamino, dialkylamino or alkylthio;

$R^5$ and $R^6$ can also together be a carbocycle which is of a ring size of $C_3$–$C_8$ and which is linked to the quinoline system via the double bond, and $R^3$ and $R^4$ are identical or different and are, independently of each other, hydrogen, alkyl which is unsubstituted or substituted by fluorine, chlorine, hydroxyl, amino, mercapto, acyloxy, benzoyloxy, benzyloxy, phenoxy, alkoxy, alkylamino, dialkylamino, alkylthio, alkylsulfonyl, alkylsulfinyl, carboxyl or carbamoyl;

alkenyl which is unsubstituted or substituted by fluorine, chlorine, hydroxyl, amino, mercapto, acyloxy, benzoyloxy, benzyloxy, phenoxy, alkoxy, alkylamino, dialkylamino, alkylthio, alkylsulfonyl, alkylsulfinyl, carboxyl or carbamoyl;

cycloalkyl which is unsubstituted or substituted by fluorine, chlorine, hydroxyl, amino, mercapto, acyloxy, benzoyloxy, benzyloxy, phenoxy, alkoxy, alkylamino, dialkylamino, alkylthio, alkylsulfonyl, alkylsulfinyl, carboxyl or carbamoyl;

cycloalkenyl which is unsubstituted or substituted by fluorine, chlorine, hydroxyl, amino, mercapto, acyloxy, benzoyloxy, benzyloxy, phenoxy, alkoxy, alkylamino, dialkylamino, alkylthio, alkylsulfonyl, alkylsulfinyl, carboxyl or carbamoyl;

or aryl or arylalkyl which is substituted by up to five radicals $R^7$ which are independent of each other, where $R^7$ is defined as above, $R^3$ and $R^4$ can also together be a carbocycle which is of a ring size of $C_3$–$C_9$ and which is linked to the quinoline system in a spiro manner;

an optical isomer or diastereomer thereof in pure form, or a mixture thereof, an addition salt thereof, or prodrug thereof, with the exception of the compounds of the formula I in which $R^1$, $R^2$, $R^5$ and $R^6$ are hydrogen, $R^3$ and $R^4$ are methyl or are together a cyclopentyl ring which is linked in a spiro manner, and X is oxygen;

the compounds of the formula I in which $R^1$ is methoxy, $R^2$ is methyl, $R^3$, $R^4$, $R^5$, and $R^6$ are hydrogen, and X is oxygen; and the compounds of the formula I in which $R^2$, $R^4$, $R^5$, and $R^6$ are hydrogen, $R^3$ is cyclopentyl, X is oxygen, and n is 0.

2. A compound of the formula I or Ia as claimed in claim 1, in which:

n is zero, one, two or three, the individual substituents $R^1$ are, independently of each other, fluorine, chlorine, bromine, iodine, trifluoromethyl, trifluoromethoxy, hydroxyl, $C_1$–$C_8$-alkyl, $C_5$–$C_8$-cycloalkyl, $C_1$–$C_8$-alkoxy, ($C_1$–$C_6$-alkoxy)-($C_1$–$C_4$-alkoxy), $C_1$–$C_6$-alkylthio, $C_1$–$C_6$-alkyl-sulfinyl, $C_1$–$C_6$-alkylsulfonyl, $C_1$–$C_6$-acyl, $C_1$–$C_6$-acyloxy, carbamoyl, carboxyl, ($C_1$–$C_6$-alkyl)-oxycarbonyl, hydroxysulfonyl or sulfamoyl, or a phenyl, phenoxy, phenoxycarbonyl, phenylthio, phenylsulfinyl, phenylsulfonyl, phenoxysulfonyl, phenyl-sulfonyloxy, phenylsulfonylamino, or benzoyl radical which is substituted by up to three radicals $R^7$ which are independent of each other.

where $R^7$ can be fluorine, chlorine, bromine, iodine, cyano, trifluoromethyl, trifluoromethoxy, nitro, amino, azido, $C_1$–$C_6$-alkyl, $C_3$–$C_8$-cycloalkyl, $C_1$–$C_6$-alkoxy, $C_1$–$C_6$-alkylthio, $C_1$–$C_6$-alkylsulfinyl, $C_1$–$C_6$-alkylsulfonyl, $C_1$–$C_6$-alkylamino, di($C_1$–$C_6$-alkyl) amino, ($C_1$–$C_6$-alkyl)-oxycarbonyl, phenyl, phenoxy or heteroaryl, X is oxygen, sulfur, or N—OH.

$R^2$ is hydrogen, alkyl which is unsubstituted or substituted by fluorine, chlorine, bromine, cyano, amino, mercapto, hydroxyl, acyloxy, benzoyloxy, benzyloxy, phenoxy, alkoxy, dialkylamino, alkylthio, alkylsulfonyl, phenylsulfonyl, oxo, thioxo, carboxyl or carbamoyl;

alkenyl which is unsubstituted or substituted by fluorine, chlorine, bromine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

alkynyl which is unsubstituted or substituted by fluorine, chlorine, bromine, mercapto, hydroxyl, acyloxy, benzoyloxy, benzyloxy, phenoxy, alkoxy, alkylamino or dialkylamino;

cycloalkyl which is unsubstituted or substituted by fluorine, chlorine, bromine, cyano, amino, mercapto, hydroxyl, acyloxy, benzoyloxy, benzyloxy, phenoxy, alkoxy, alkylamino or dialkylamino;

cycloalkenyl which is unsubstituted or substituted by fluorine, chlorine, bromine, cyano, amino, mercapto, hydroxyl, acyloxy, benzoyloxy, benzyloxy, phenoxy, alkoxy, alkylamino or dialkylamino;

(cycloalkyl)-(alkyl) which is unsubstituted or substituted by fluorine, chlorine, bromine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

(cycloalkenyl)-(alkyl) which is unsubstituted or substituted by fluorine, chlorine, bromine, cyano, amino, mercapto, hydroxyl, acyloxy, benzoyloxy, benzyloxy, phenoxy, alkoxy, alkylthio, alkylsulfonyl or phenylsulfonyl;

$R^5$ and $R^6$ are identical or different and are, independently of each other, hydrogen, $C_1$–$C_8$-alkyl which is unsubstituted or substituted by fluorine, chlorine, bromine, iodine, cyano, amino, mercapto, hydroxyl, $C_1$–$C_6$-acyloxy, benzoyloxy, benzyloxy, phenoxy, $C_1$–$C_6$-alkoxy, $C_1$–$C_6$-alkylamino, di($C_1$–$C_6$-alkyl)amino, $C_1$–$C_6$-alkylthio, $C_1$–$C_6$-alkyl-sulfonyl, phenylsulfonyl, oxo, thioxo, carboxyl or carbamoyl;

$C_2$–$C_8$-alkenyl which is unsubstituted or substituted by fluorine, chlorine, bromine, iodine, cyano, amino, mercapto, hydroxyl, $C_1$–$C_6$-acyloxy, benzoyloxy, benzyloxy, phenoxy, $C_1$–$C_6$-alkoxy, $C_1$–$C_6$-alkylamino, di($C_1$–$C_6$-alkyl)amino, $C_1$–$C_6$-alkylthio, $C_1$–$C_6$-alkylsulfonyl, phenylsulfonyl, oxo, thioxo, carboxyl or carbamoyl;

$C_3$–$C_8$-alkynyl which is unsubstituted or substituted by fluorine, chlorine, bromine, iodine, cyano, amino, mercapto, hydroxyl, $C_1$–$C_6$-acyloxy, benzoyloxy, benzyloxy, phenoxy, $C_1$–$C_6$-alkoxy, $C_1$–$C_6$-alkylamino, di($C_1$–$C_6$-alkyl)amino, $C_1$–$C_6$-alkylthio, $C_1$–$C_6$-alkyl-sulfonyl, phenylsulfonyl, oxo, thioxo, carboxyl or carbamoyl;

$C_3$–$C_8$-cycloalkyl which is unsubstituted or substituted by fluorine, chlorine, bromine, iodine, cyano, amino, mercapto, hydroxyl, $C_1$–$C_6$-acyloxy, benzoyloxy, benzyloxy, phenoxy, $C_1$–$C_6$-alkoxy, $C_1C_6$-alkylamino, di($C_1$–$C_6$-alkyl)amino, $C_1$–$C_6$-alkylthio, $C_1$–$C_6$-alkylsulfonyl, phenylsulfonyl, oxo, thioxo, carboxyl or carbamoyl;

$C_5$–$C_8$-cycloalkenyl which is unsubstituted or substituted by fluorine, chlorine, bromine, iodine, cyano, amino, mercapto, hydroxyl, $C_1$–$C_6$-acyloxy, benzoyloxy, benzyloxy, phenoxy, $C_1$–$C_6$-alkoxy, $C_1$–$C_6$-alkylamino, di($C_1$–$C_6$-alkyl)amino, $C_1$–$C_6$-alkylthio, $C_1$–$C_6$-alkylsulfonyl, phenylsulfonyl, oxo, thioxo, carboxyl or carbamoyl;

($C_3$–$C_8$-cycloalkyl)-($C_1$–$C_4$-alkyl) which is unsubstituted or substituted by fluorine, chlorine, bromine, iodine, cyano, amino, mercapto, hydroxyl, $C_1$–$C_6$-acyloxy, benzoyloxy, benzyloxy, phenoxy, $C_1$–$C_6$-alkoxy, $C_1$–$C_6$-alkylamino, di-($C_1$–$C_6$-alkyl)amino, $C_1$–$C_6$-alkylthio, $C_1$–$C_6$-alkylsulfonyl, phenylsulfonyl, oxo, thioxo, carboxyl or carbamoyl;

($C_5$–$C_8$-cycloalkenyl)-($C_1$–$C_4$-alkyl) which is unsubstituted or substituted by fluorine, chlorine, bromine, iodine, cyano, amino, mercapto, hydroxyl, $C_1$–$C_6$-acyloxy, benzoyloxy, benzyloxy, phenoxy, $C_1$–$C_6$-alkoxy, $C_1$–$C_6$-alkylamino, di($C_1$–$C_6$-alkyl)amino, $C_1$–$C_6$-alkylthio, $C_1$–$C_6$-alkylsulfonyl, phenylsulfonyl, oxo, thioxo, carboxyl or carbamoyl;

$C_1$–$C_8$-alkyloxycarbonyl which is unsubstituted or substituted by fluorine, chlorine, bromine, hydroxyl, $C_1$–$C_1$-alkoxy, $C_1$–$C_4$-alkylamino, di($C_1$–$C_4$-alkyl)amino or $C_1$–$C_4$-alkylthio;

$R^5$ and $R^6$ can also together be a carbocycle which is of a ring size of $C_3$–$C_8$ and which is linked to the quinoline system via the double bond, and $R^3$ and $R^4$ are identical or different and are, independently of each other, hydrogen, $C_1$–$C_8$-alkyl which is unsubstituted or substituted by fluorine, chlorine, hydroxyl, amino, mercapto, $C_1$–$C_4$-acyloxy, benzoyloxy, benzyloxy, phenoxy, $C_1$–$C_4$-alkoxy, $C_1$–$C_4$-alkylamino, di($C_1$–$C_4$-alkyl)amino, $C_1$–$C_4$-alkylthio, $C_1$–$C_4$-alkylsulfonyl, $C_1$–$C_4$-alkylsulfinyl, carboxyl or carbamoyl;

$C_2$–$C_8$-alkenyl which is unsubstituted or substituted by fluorine or chlorine, hydroxyl, amino, mercapto, $C_1$–$C_4$-acyloxy, benzoyloxy, benzyloxy, phenoxy, $C_1$–$C_4$-alkoxy, $C_1$–$C_4$-alkylamino, di($C_1$–$C_4$-alkyl)amino, $C_1$–$C_4$-alkylthio, $C_1$–$C_4$-alkylsulfonyl, $C_1$–$C_4$-alkylsulfinyl, carboxyl or carbamoyl;

$C_3$–$C_8$-cycloalkyl which is unsubstituted or substituted by fluorine or chlorine, hydroxyl, amino, mercapto, $C_1$–$C_4$-acyloxy, benzoyloxy, benzyloxy, phenoxy, $C_1$–$C_4$-alkoxy, $C_1$–$C_4$-alkylamino, di($C_1$–$C_4$-alkyl) amino, $C_1$–$C_4$-alkylthio, $C_1$–$C_4$-alkylsulfonyl, $C_1$–$C_4$-alkylsulfinyl, carboxyl or carbamoyl;

$C_3$–$C_8$-cycloalkenyl which is unsubstituted or substituted by fluorine or chlorine, hydroxyl, amino, mercapto, $C_1$–$C_4$-acyloxy, benzoyloxy, benzyloxy, phenoxy, $C_1$–$C_4$-alkoxy, $C_1$–$C_4$-alkylamino, di($C_1$–$C_4$-alkyl) amino, $C_1$–$C_4$-alkylthio, $C_1$–$C_4$-alkylsulfonyl, $C_1$–$C_4$-alkylsulfinyl, carboxyl or carbamoyl;

aryl or arylalkyl which is substituted by up to three radicals $R^7$ which are independent of each other, where the alkyl radical can in each case contain from 1 to 3 carbon atoms and $R^7$ is defined as above;

$R^3$ and $R^4$ can also, in structures of the formulae I and Ia, together be a carbocycle which is of a ring size of $C_3$–$C_8$ and which is linked to the quinoline system in a spiro manner.

3. A compound of the formula I or Ia as claimed in claim 1, in which:

n is zero, one or two, the individual substituents $R^1$ are, independently of each other, fluorine, chlorine, bromine, trifluoromethyl, trifluoromethoxy, hydroxyl, $C_1$–$C_6$-alkyl, $C_5$–$C_6$-cycloalkyl, $C_1$–$C_6$-alkoxy, ($C_1$–$C_6$-alkoxy)-($C_1$–$C_2$-alkoxy), $C_1$–$C_4$-alkylthio, $C_1$–$C_4$-alkylsulfinyl, $C_1$–$C_4$-alkylsulfonyl, $C_1$–$C_6$-acyloxy, $C_1$–$C_4$-acyloxy, carbamoyl, carboxyl or ($C_1$–$C_4$-alkyl)oxycarbonyl, or a phenyl, phenoxy, phenoxycarbonyl, phenylthio, phenylsulfinyl, phenylsulfonyl, phenoxysulfonyl, phenylsulfonyloxy, phenylsulfonylamino, or benzoyl radical which is substituted by up to two radicals $R^7$ which are independent of each other, where $R^7$ is fluorine, chlorine, trifluoromethyl, trifluoromethoxy, nitro, amino, $C_1$–$C_4$-alkyl, $C_3C_6$-cycloalkyl, $C_1$–$C_4$-alkoxy, $C_1$–$C_4$-alkylthio, $C_1$–$C_4$-alkylsulfinyl, $C_1$–$C_4$-alkylsulfonyl, $C_1$–$C_4$-alkylamino, or di($C_1$–$C_4$-alkyl)amino, X is oxygen, sulfur, or N—OH, $R^2$ is hydrogen, alkyl which is unsubstituted or substituted by fluorine, chlorine, cyano, amino, mercapto, hydroxyl, acyloxy, benzoyloxy, benzyloxy, phenoxy, alkoxy, dialkylamino, alkylthio, alkylsulfonyl, phenylsulfonyl, oxo, thioxo or carboxyl;

alkenyl which is unsubstituted or substituted by fluorine, chlorine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo or carboxyl;

alkynyl;

cycloalkyl;

cycloalkenyl;

(cycloalkyl)-(alkyl) which is unsubstituted or substituted by fluorine, chlorine, bromine, amino, mercapto, hydroxyl, acyloxy, benzoyloxy, benzyloxy, phenoxy, alkoxy, alkylamino, dialkylamino, alkylthio, alkylsulfonyl or phenylsulfonyl;

(cycloalkenyl)-(alkyl);

$R^5$ and $R^6$ are identical or different and are, independently of each other, hydrogen, $C_1$–$C_6$-alkyl which is unsubstituted or substituted by fluorine, chlorine, bromine, iodine, cyano, amino, mercapto, hydroxyl, $C_1$–$C_4$-acyloxy, benzoyloxy, benzyloxy, phenoxy, $C_1$–$C_4$-alkoxy, $C_1$–$C_4$-alkylamino, di($C_1$–$C_4$-alkyl)amino, $C_1$–$C_4$-alkylthio, $C_1$–$C_4$-alkylsulfonyl, phenylsulfonyl, oxo, thioxo, carboxyl or carbamoyl;

$C_2$–$C_6$-alkenyl which is unsubstituted or substituted by fluorine, chlorine, cyano, amino, mercapto, hydroxyl, $C_1$–$C_4$-acyloxy, benzoyloxy, benzyloxy, phenoxy, $C_1$–$C_4$-alkoxy, $C_1$–$C_4$-alkylamino, di($C_1$–$C_4$-alkyl) amino, $C_1$–$C_4$-alkylthio, $C_1$–$C_4$-alkylsulfonyl, phenylsulfonyl, carboxyl or carbamoyl;

$C_3$–$C_6$-alkynyl which is unsubstituted or substituted by fluorine, chlorine, cyano, amino, mercapto, hydroxyl, $C_1$–$C_4$-acyloxy, benzoyloxy, benzyloxy, phenoxy, $C_1$–$C_4$-alkoxy, $C_1$–$C_4$-alkylamino, di($C_1$–$C_4$-alkyl) amino, $C_1$–$C_4$-alkylthio, $C_1$–$C_4$-alkylsulfonyl, phenylsulfonyl, carboxyl or carbamoyl;

$C_3$–$C_6$-cycloalkyl which is unsubstituted or substituted by fluorine, chlorine, cyano, amino, mercapto, hydroxyl, $C_1$–$C_4$-acyloxy, benzoyloxy, benzyloxy, phenoxy, $C_1$–$C_4$-alkoxy, $C_1$–$C_4$-alkylamino, di($C_1$–$C_4$-alkyl) amino, $C_1$–$C_4$-alkylthio, $C_1$–$C_4$-alkylsulfonyl, phenylsulfonyl, carboxyl or carbamoyl;

$C_5$–$C_6$-cycloalkenyl which is unsubstituted or substituted by fluorine, chlorine, cyano, mercapto, hydroxyl, $C_1$–$C_4$-acyloxy, benzoyloxy, benzyloxy, phenoxy, $C_1$–$C_4$-alkoxy, $C_1$–$C_4$-alkylthio, $C_1$–$C_4$-alkylsulfonyl, phenylsulfonyl, carboxyl or carbamoyl;

($C_3$–$C_6$-cycloalkyl)-($C_1$–$C_2$-alkyl) which is unsubstituted or substituted by fluorine, chlorine, cyano, amino, mercapto, hydroxyl, $C_1$–$C_4$-acyloxy, benzoyloxy, benzyloxy, phenoxy, $C_1$–$C_4$-alkoxy, $C_1$–$C_4$-alkylthio or carboxyl;

($C_5$–$C_6$-cycloalkenyl)-($C_1$–$C_2$-alkyl) which is unsubstituted or substituted by fluorine, chlorine, cyano, amino, mercapto, hydroxyl, $C_1$–$C_4$-acyloxy, benzoyloxy, benzyloxy, phenoxy, $C_1$–$C_4$-alkoxy, $C_1$–$C_4$-alkylthio or carboxyl;

$C_1$–$C_6$-alkyloxycarbonyl which is unsubstituted or substituted by fluorine, chlorine, $C_1$–$C_4$-alkoxy, $C_1$–$C_4$-alkylamino, di($C_1$–$C_4$-alkyl)amino or $C_1$–$C_4$-alkylthio; and $R^5$ and $R^6$ can also together be a carbocycle which is of a ring size of $C_5$–$C_6$ and which is linked to the quinoline system via the double bond, $R^3$ and $R^4$ are identical or different and are, independently of each other, $C_1$–$C_6$-alkyl which is unsubstituted or substituted by fluorine, chlorine, hydroxyl, amino, mercapto, $C_1$–$C_4$-acyloxy, benzoyloxy, benzyloxy, phenoxy, $C_1$–$C_4$-alkoxy, $C_1$–$C_4$-alkyl-amino, di($C_1$–$C_4$-alkyl)amino, $C_1$–$C_4$-alkylthio, $C_1$–$C_4$-alkylsulfonyl, $C_1$–$C_4$-alkylsulfinyl, carboxyl or carbamoyl;

$C_2$–$C_6$-alkenyl which is unsubstituted or substituted by fluorine or chlorine, phenoxy, $C_1$–$C_4$-alkoxy, $C_1$–$C_4$-alkylthio, $C_1$–$C_4$-alkylsulfonyl or $C_1$–$C_4$-alkylsulfinyl;

$C_3$–$C_6$-cycloalkyl which is unsubstituted or substituted by fluorine, chlorine, hydroxyl, amino, mercapto, $C_1$–$C_4$-acyloxy, benzoyloxy, benzyloxy, phenoxy, $C_1$–$C_4$-alkoxy, $C_1$–$C_4$-alkylamino, di($C_1$–$C_4$-alkyl)amino, $C_1$–$C_4$-alkylthio, $C_1$–$C_4$-alkylsulfonyl or $C_1$–$C_4$-alkylsulfinyl;

$C_3$–$C_6$-cycloalkenyl which is unsubstituted or substituted by fluorine or chlorine, phenoxy, $C_1$–$C_4$-alkoxy, $C_1$–$C_4$-alkylthio, $C_1$–$C_4$-alkylsulfonyl or $C_1$–$C_4$-alkylsulfinyl;

aryl or arylalkyl which is substituted by up to three radicals $R^7$ which are independent of each other, where the alkyl radical can in each case contain from 1 to 3 carbon atoms and $R^7$ is defined as above, it being possible for one of the radicals $R^3$ or $R^4$ to be hydrogen, $R^3$ and $R^4$ can also, in structures of the formulae I and Ia, together be a carbocycle which is of a ring size of $C_4C_6$ and which is linked to the quinoline system in a spiro manner.

4. A compound of the formula I or Ia as claimed in claim 1, in which:

n is zero, one or two, the individual substituents $R^1$ are, independently of each other, fluorine, chlorine, trifluoromethyl, trifluoromethoxy, hydroxyl, $C_1$–$C_4$-alkyl, $C_1$–$C_4$-alkoxy, ($C_1$–$C_4$-alkoxy)-($C_1$–$C_2$-alkoxy), $C_1$–$C_4$-alkylthio, $C_1$–$C_4$-alkyl-sulfinyl, $C_1$–$C_4$-alkylsulfonyl, $C_1$–$C_4$-acyl, $C_1$–$C_4$-acyloxy, carbamoyl, carboxyl or ($C_1$–$C_4$-alkyl)-oxycarbonyl, or a phenyl, phenoxy, phenoxycarbonyl, phenylthio, phenylsulfinyl, phenylsulfonyl, or benzoyl radical;

X is oxygen, sulfur or N—OH, $R^2$ is hydrogen or ($C_1$–$C_4$)-alkyl;

($C_2$–$C_5$)-alkenyl;

$R^5$ and $R^6$ are identical or different and are, independently of each other, hydrogen, $C_1$–$C_6$-alkyl which is unsubstituted or substituted by fluorine, chlorine, amino, mercapto, hydroxyl, $C_1$–$C_4$-acyloxy, benzoyloxy, benzyloxy, phenoxy, $C_1$–$C_4$-alkoxy, $C_1$–$C_4$-alkylamino, di($C_1$–$C_4$-alkyl)amino or $C_1$–$C_4$-alkylthio;

$C_2$–$C_6$-alkenyl which is unsubstituted or substituted by fluorine, chlorine, amino, mercapto, hydroxyl, $C_1$–$C_4$-acyloxy, benzoyloxy, benzyloxy, phenoxy, $C_1$–$C_4$-alkoxy, $C_1$–$C_4$-alkylamino, di($C_1$–$C_4$-alkyl)amino or $C_1$–$C_4$-alkylthio;

$C_3$–$C_6$-cycloalkyl, $C_5$–$C_6$-cycloalkenyl, ($C_3$–$C_6$-cycloalkyl)-($C_1$–$C_2$-alkyl), ($C_5$–$C_6$-cycloalkenyl)-($C_1$–$C_2$-alkyl), $C_1$–$C_6$-alkyloxycarbonyl which is unsubstituted or substituted by $C_1$–$C_4$-alkylamino, di($C_1$–$C_4$-alkyl)amino or $C_1$–$C_4$-alkylthio; and $R^5$ and $R^6$ can also together be a carbocycle which is of a ring size of $C_5$–$C_6$ and which is linked to the quinoline system via the double bond, $R^3$ and $R^4$ are identical or different and are, independently of each other, $C_1$–$C_6$-alkyl which is unsubstituted or substituted by fluorine, chlorine, hydroxyl, amino, mercapto, $C_1$–$C_4$-acyloxy, benzoyloxy, benzyloxy, phenoxy, $C_1$–$C_4$-alkoxy, $C_1$–$C_4$-alkyl-amino, di($C_1$–$C_4$-alkyl)amino, $C_1$–$C_4$-alkylthio, $C_1$–$C_4$-alkylsulfonyl, $C_1$–$C_4$-alkyl-sulfinyl or carboxy, $C_2$–$C_6$-alkenyl which is unsubstituted or substituted by fluorine or chlorine;

$C_3$–$C_6$-cycloalkyl, $C_5$–$C_6$-cycloalkenyl which is unsubstituted or substituted by fluorine or chlorine;

with it also being possible for one of the radicals $R^3$ and $R^4$ to be hydrogen;

$R^3$ and $R^4$ can also, in structures of the formulae I and Ia, together be a carbocycle which is of a ring size of $C_4$–$C_6$ and which is linked to the quinoline system in a spiro manner.

5. A compound of the formula I or Ia as claimed in claim 1, in which:

n is zero, one or two, the individual substituents $R^1$ are, independently of each other, fluorine, chlorine, trifluoromethoxy, hydroxyl, $C_1$–$C_4$-alkoxy or $C_1$–$C_4$-alkylthio, X is oxygen, sulfur or N—OH, $R^2$ is hydrogen;

$R^5$ and $R^6$ are identical or different and are, independently of each other, hydrogen, $C_1$–$C_6$-alkyl which is unsubstituted or substituted by fluorine, chlorine, amino, mercapto, hydroxyl, $C_1$–$C_4$-acyloxy, benzoyloxy, benzyloxy, phenoxy, $C_1$–$C_4$-alkoxy, $C_1$–$C_4$-alkylamino, di($C_1$–$C_4$-alkyl)amino or $C_1$–$_4$-alkylthio;

$C_2$–$C_6$-alkenyl which is unsubstituted or substituted by fluorine, chlorine, amino, mercapto, hydroxyl, $C_1$–$C_4$-acyloxy, benzoyloxy, benzyloxy, phenoxy, $C_1$–$C_4$-alkoxy, $C_1$–$C_4$-alkylamino, di($C_1$–$C_4$-alkyl)amino or $C_1$–$C_4$-alkylthio;

$R^5$ and $R^6$ can also together be a carbocycle which is of a ring size of $C_5$–$C_6$ and which is linked to the quinoline system via the double bond, and $R^3$ and $R^4$ are identical or different and are, independently of each other, $C_1$–$C_2$-alkyl;

$R^3$ and $R^4$ can also, in structures of the formulae I and Ia, together be a carbocycle which is of a ring size of $C_4$–$C_6$ and which is linked to the quinoline system in a spiro manner.

6. A pharmaceutical composition comprising an effective amount of a compound of the formula I,

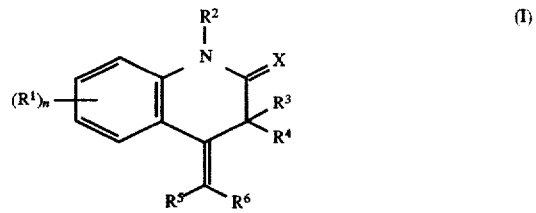

(I)

and also its tautomeric forms of the formula Ia,

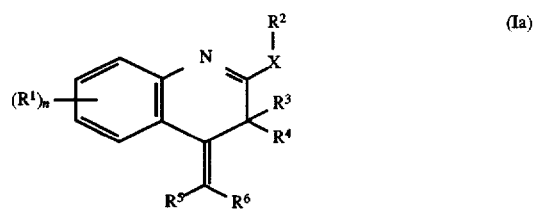

(Ia)

in which:

n is zero, one, two, three or four, the individual substituents $R^1$ are, independently of each other, fluorine, chlorine, bromine, iodine, trifluoromethyl, trifluoromethoxy, hydroxyl, alkyl, cycloalkyl, alkoxy, alkoxy(alkoxy), alkylthio, alkylsulfinyl, alkylsulfonyl, acyl, acyloxy, carbamoyl, carboxyl, alkyloxycarbonyl, hydroxy-sulfonyl or sulfamoyl, or a phenyl, phenoxy, phenoxycarbonyl, phenylthio, phenylsulfinyl, phenylsulfonyl, phenoxysulfonyl, phenylsulfonyloxy, anilinosulfonyl, phenylsulfonylamino, or benzoyl radical which is substituted by up to five radicals $R^7$ which are independent of each other, where $R^7$ can be fluorine, chlorine, bromine, iodine, cyano, trifluoromethyl, trifluoromethoxy, nitro, amino, azido, alkyl, cycloalkyl, alkoxy, alkylthio, alkylsulfinyl, alkylsulfonyl, alkylamino, dialkylamino, or alkyloxycarbonyl, X is oxygen, sulfur, or N—OH $R^2$ is hydrogen or alkyl which is unsubstituted or substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl or alkoxycarbonyl;

alkenyl which is unsubstituted or substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

alkynyl which is unsubstituted or substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

cycloalkyl which is unsubstituted or substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

cycloalkenyl which is unsubstituted or substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

(cycloalkyl)-(alkyl) which is unsubstituted or substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

(cycloalkenyl)-(alkyl) which is unsubstituted or substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

$R^5$ and $R^6$ are identical or different and are, independently of each other, hydrogen, carboxyl, alkyl which is unsubstituted or substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl or alkoxycarbonyl;

alkenyl which is unsubstituted or substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

alkynyl which is unsubstituted or substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

cycloalkyl which is unsubstituted or substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

cycloalkenyl which is unsubstituted or substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

(cycloalkyl)-(alkyl) which is unsubstituted or substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

(cycloalkenyl)-(alkyl) which is unsubstituted or substituted by fluorine, chlorine, bromine, iodine, cyano, amino, mercapto, hydroxyl, acyloxy, benzoyloxy, phenoxy, alkoxy, alkylamino, dialkylamino, alkylthio, alkylsulfonyl, phenylsulfonyl, oxo, thioxo, carboxyl or carbamoyl;

alkyloxycarbonyl which is unsubstituted or substituted by fluorine, chlorine, bromine, hydroxyl, alkoxy, alkylamino, dialkylamino or alkylthio;

$R^5$ and $R^6$ can also together be a carbocycle which is of a ring size of $C_3$–$C_8$ and which is linked to the quinoline system via the double bond, and $R^3$ and $R^4$ are identical or different and are, independently of each other, hydrogen, alkyl which is unsubstituted or substituted by fluorine, chlorine, hydroxyl, amino, mercapto, acyloxy, benzoyloxy, benzyloxy, phenoxy, alkoxy, alkylamino, dialkylamino, alkylthio, alkylsulfonyl, alkylsulfinyl, carboxyl or carbamoyl;

alkenyl which is unsubstituted or substituted by fluorine, chlorine, hydroxyl, amino, mercapto, acyloxy, benzoyloxy, benzyloxy, phenoxy, alkoxy, alkylamino, dialkylamino, alkylthio, alkylsulfonyl, alkylsulfinyl, carboxyl or carbamoyl;

cycloalkyl which is unsubstituted or substituted by fluorine, chlorine, hydroxyl, amino, mercapto, acyloxy, benzoyloxy, benzyloxy, phenoxy, alkoxy, alkylamino, dialkylamino, alkylthio, alkylsulfonyl, alkylsulfinyl, carboxyl or carbamoyl;

cycloalkenyl which is unsubstituted or substituted by fluorine, chlorine, hydroxyl, amino, mercapto, acyloxy, benzoyloxy, benzyloxy, phenoxy, alkoxy, alkylamino, dialkylamino, alkylthio, alkylsulfonyl, alkylsulfinyl, carboxyl or carbamoyl;

or aryl or arylalkyl which is substituted by up to five radicals $R^7$ which are independent of each other, where $R^7$ is defined as above, $R^3$ and $R^4$ can also together be a carbocycle which is of a ring size of $C_3$–$C_8$ and which is linked to the quinoline system in a spiro manner, an optical isomer or diastereomer thereof in pure form, or a mixture thereof, an addition salt thereof, or prodrug thereof, together with at least one of a auxiliary substance and a carrier.

7. A method for treating viral diseases which comprises administering an effective amount of a compound of the formulae I or Ia as claimed in claim 1.

8. A process for preparing pharmaceuticals, wherein a compound of the formulae I or Ia as claimed in claim 1 and, where appropriate an auxiliary substance and a carrier substance, is brought into a suitable form for administration.

9. A process for preparing compounds of the formulae I or Ia as claimed in claim 1, wherein A) in order to prepare compounds of the formula I in which X is oxygen and Ia in which X is defined as in claim 1—with the exception of N—$R^2$ being N—H—and the radicals $R^1$, $R^2$, $R^3$, $R^4$, $R^5$ and $R^6$ are defined as in claim 1, a compound of the formulae II and IIa,

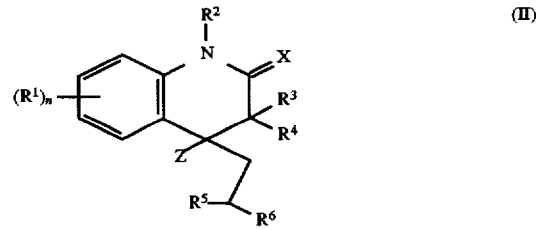

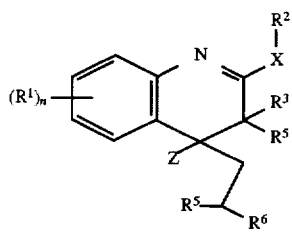

(IIa)

in which Z is a leaving group or an hydroxyl group, is heated in an inert solvent, where appropriate with an acidic or basic catalyst being added, B) in order to prepare compounds of the formula II in which X is oxygen and Z is hydroxyl and IIa in which Z is hydroxyl, X is defined as in claim 1—with the exception of N—$R^2$ being N—H— and the radicals $R^1$, $R^2$, $R^3$, $R^4$, $R^5$ and $R^6$ are defined as in claim 1, a compound of the formula III or IIIa,

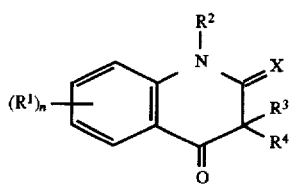

(III)

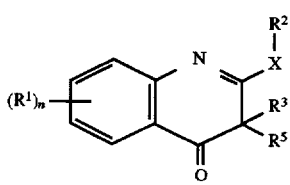

(IIIa)

is reacted with a compound of the formula IV

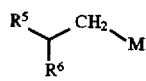

IV where M is a metal atom equivalent such as Li, —MgCl or —MgBr, or

C) in order to prepare compounds of the formula I in which X is sulfur and $R^1$, $R^2$, $R^3$, $R^4$, $R^5$ and $R^6$ are defined as in claim 1, by means of reacting a compound of the formula I, where X is oxygen and the definitions mentioned in claim 1 apply to $R^1$, $R^2$, $R^3$, $R^4$, $R^5$ and $R^6$, with a sulfurization reagent, or wherein D) compounds of the formula I in which X is oxygen, $R^2$ is hydrogen and $R^1$, $R^3$, $R^4$, $R^5$ and $R^6$ are defined as in claim 1, are prepared by reacting with an alkylating reagent of the formula V

  V where $R^2$ has the meanings given in claim 1, with the exception of $R^2$ being hydrogen, and the leaving group K is a halogen atom or is a sulfonic ester group, or wherein E) a compound of the formula I in which $R^1$–$R^6$ are defined as in claim 1 and X is an oxygen atom or a sulfur atom is reacted with a compound of the formula

to form derivatives of the formula I in which $R^1$–$R^6$ are defined as in claim 1 and X is N—$R^2$ or N—O—$R^2$, or wherein F) a compound of the formula I in which $R^1$–$R^6$ are defined as in claim 1, with one of these radicals possessing an alkoxycarbonyl group, is reacted with a compound of the formula

in which Met is an alkali metal atom or alkaline earth metal atom, to form derivatives of the formula I which possess a free carboxylic acid function, or wherein G) a compound of the formula I in which $R^1$=methoxy and $R^2$–$R^6$ are defined as in claim 1 and X is oxygen is reacted with trimethylsilyl iodide to form a compound of the formula I in which $R^1$=hydroxyl and the radicals $R^2$–$R^6$ and X are defined as above.

10. A method for treating viral diseases which comprises administering a pharmaceutical composition as claimed in claim 6.

* * * * *

UNITED STATES PATENT AND TRADEMARK OFFICE
CERTIFICATE OF CORRECTION

PATENT NO. : 5,798,365
DATED : August 25, 1998
INVENTOR(S) : Kirsch et al.

Page 1 of 2

It is certified that error appears in the above-identified patent and that said Letters Patent is hereby corrected as shown below:

Claim 2, column 101, line 62, "$C_1C_6$-alkylamino" should read --$C_1$-$C_6$-alkylamino--.
Claim 3, column 103, line 4, "$C_1$-$C_6$-acyloxy" should read --$C_1$-$C_6$-acyl--.
Claim 3, column 103, lines 12-13, "$C_3C_6$-cycloalkyl" should read --$C_3$-$C_6$-cycloalkyl--.
Claim 3, column 104, line 50, "$C_4C_6$" should read --$C_4$-$C_6$--.
Claim 4, column 105, line 32, "carboxy," should read --carboxyl;--.
Claim 4, column 105, line 40, "$R^4$ to" should read --" $R^4$ to--.
Claim 6, column 106, line 49, after "N-OH", insert --,--.
Claim 6, column 108, line 41, "a auxiliary" should read --an auxiliary--.
Claim 9, column 109, lines 1-10, in formula (IIa), " 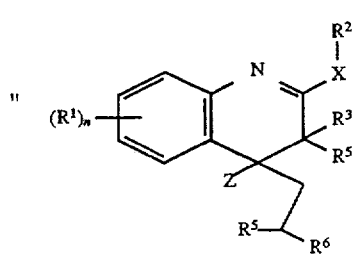  should read -- 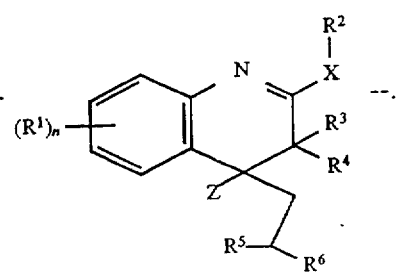 --.

UNITED STATES PATENT AND TRADEMARK OFFICE
CERTIFICATE OF CORRECTION

PATENT NO. : 5,798,365
DATED : August 25, 1998
INVENTOR(S) : Kirsch et al.

It is certified that error appears in the above-identified patent and that said Letters Patent is hereby corrected as shown below:

Claim 9, column 109, line 12, "an hydroxyl" should read --a hydroxyl--.
Claim 9, column 109, lines 29-35, in formula (IIIa),

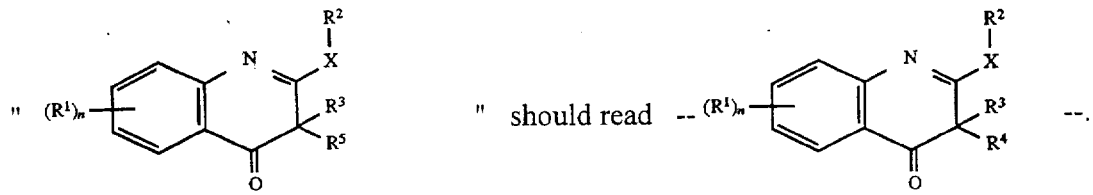

Signed and Sealed this

Twenty-seventh Day of June, 2000

*Attest:*

Q. TODD DICKINSON

*Attesting Officer*   *Director of Patents and Trademarks*